US006074832A

United States Patent [19]
Venta et al.

[11] Patent Number: 6,074,832
[45] Date of Patent: *Jun. 13, 2000

[54] DNA ENCODING CANINE VON WILLEBRAND FACTOR AND METHODS OF USE

[75] Inventors: Patrick J. Venta, Pinckney; George J. Brewer; Vilma Yuzbasiyan-Gurkan, both of Ann Arbor; William D. Schall, Williamston; John Duffendeck, Ann Arbor, all of Mich.

[73] Assignee: The Regents of the University of Michigan, Ann Arbor, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 09/132,652

[22] Filed: Aug. 11, 1998

Related U.S. Application Data

[63] Continuation-in-part of application No. 08/896,449, Jul. 18, 1997.
[60] Provisional application No. 60/020,998, Jul. 19, 1996.
[51] Int. Cl.[7] .............................. C12Q 1/70; C12P 19/34; C07H 21/04; C12N 1/20
[52] U.S. Cl. .......................... 435/6; 435/91.2; 435/252.3; 435/325; 536/22.1; 536/24.3
[58] Field of Search .......................... 435/6, 91.2, 252.3, 435/325; 536/22.1, 24.3

[56] References Cited

PUBLICATIONS

Avgeris, S. et al., "Plasma von Willebrand Factor Concentration and Thyroid Function in Dogs," *JAVMA* 196:921–92 (1990).
Bakhshi, M.R. et al., "Sequencing of the Primary Adhesion Domain of Bovine von Willebrand Factor," *Biochem. Biophys. Acta* 1132:325–328 (1992).
Benson, R.E. et al., "Efficiency and Precision of Electroimmunoassay for Canine Factor VIII–Related Antigen," *Am. J. Vet. Res*. 44:399–403 (1983).
Bergenhem, N.C.H. et al., "Mutation Creates an Open Reading Frame within the 5' Untranslated Region of Macaque Erythrocyte Carbonic Anhydrase (CA) I mRNA that Suppresses CA I Expression and Supports the Scanning Model for Translation," *PNAS (USA)* 89:8789–8802 (1992).
Bloom, A.L., "Von Willebrand Factor: Clinical Features of Inherited and Acquired Disorders," *Mayo Clin. Proc.* 66:743–751 (1991).
Bonthron, D. et al., "Nucleotide Sequence of Pre–Pro–von Willebrand Factor cDNA," *Nucleic Acids Res.* 14:7125–7127 (1986).
Brinkhous, K.M. et al., "Pathophysiology of Platelet–Aggegating von Willebrand Factor: Applications of the Venom Coagglutinin vWF Assay," *Ann. New York Acad. Sci.* 370:191–204 (1981).
Brooks, M., "Clinical Features of Canine von Willebrand's Disease," *Proc. 9th ACVIM Forum* pp. 89–91 (1991).

Brooks, M., "Management of Canine von Willebrand's Disease," *Probl. In Vet. Med.* 4:636–646 (1992).
Brooks, M. et al., "Epidemiologic Features of von Willebrand's Disease in Doberman Pinschers, Scottish Terriers, and Shetland Sheepdogs: 260 Cases (1984–1988)," *JAVMA* 200:1123–1127 (1992).
Dodds, W.J., "Von Willebrand's Disease in Dogs," *Mod. Vet. Pract.* 681–686 (1984).
Ginsburg, D. et al., "Molecular Genetics of von Willebrand's Disease," *Blood* 79:2507–2519 (1992).
Janel, N. et al., "Comparison of the 5'–Flanking sequences of the Human and Bovine von Willebrand Factor–Encoding Genes Reveals Alternation of Highly Homologous Domains with Species–Specific *Alu*–Type Repeats," *Gene* 167:291–295 (1995).
Johnson, G.S. et al., "A Bleeding Disease (von Willebrand's Disease) in a Chesapeake Bay Retriever," *JAVMA* 176:1261–1263 (1980).
Kraus, K.H. et al., "Effect of Desmopressin Acetate on Bleeding Times and Plasma von Willebrand Factor in Doberman Pinscher Dogs with von Willebrand's Disease," *Vet. Surg.* 18:103–109 (1989).
Lankhof, H. et al., "Role of the Glycoprotein Ib–Binding A1 Repeat and the RGD Sequence in Platelet Adhesion to Human Recombinant von Willebrand Factor," *Blood* 86:1035–1042 (1995).
Lavergne, J.M. et al., "Primary Structure of the Factor VIII Binding Domain of Human, Porcine and Rabbit von Willebrand Factor," *Biochem. Biophys. Res. Commun.* 194:1019–1024 (1993).
Mancuso, D.J. et al., "Human von Willebrand Factor Gene and Pseudogene: Structural Analysis and Differentiation by Polymerase Chain Reaction," *Biochemistry* 30:253–269 (1991).
Mancuso, D.J. et al., 1576 An Homologous Canine von Willebrand and Factor Binding Domain for Glycoprotein Ib; *Thromb Haemost* 69:980 (1993).
Maniatis, T., et al., *Molecular Cloning: A Laboratory Manual, Cold Springs Harbor Laboratory Press*, Cold Spring NY, (1982), at pp. 387–389.
Mansell, P.D. et al., "Changes in Factor VIII Activity and von Willebrand Factor Antigen Concentration with Age in Dogs," *Br. Vet. J.* 148:329–337 (1992).
Meyer, D. et al., "von Willebrand Factor: Structure and Function," *Throm. Haemostasis* 70:99–104 (1993).

(List continued on next page.)

*Primary Examiner*—Ardin H. Marschel
*Assistant Examiner*—Joyce Tung
*Attorney, Agent, or Firm*—Lahive & Cockfield, LLP

[57] ABSTRACT

The complete sequence of the canine von Willebrand Factor cDNA and deduced amino acid sequence is provided. The mutation which causes von Willebrand's Disease in Scottish Terriers, Doberman pinschers, Shetland sheepdogs, Manchester terriers and Poodles are also provided. Methods for detecting carriers of the defective vWF gene are also provided.

17 Claims, 21 Drawing Sheets

OTHER PUBLICATIONS

O'Brien, P.J. et al., "Use of a DNA–Based Test for the Mutation Associated with Porcine Stress Syndrome (Malignant Hyperthermia) in 10,000 Breeding Swine," *JAVMA* 203:842–851 (1993).

Panciera, D.L. et al., "Plasma von Willebrand Factor Antigen Concentration in Dogs with Hypothyroidism," *JAVMA* 205:1550–1553 (1994).

Porter, C.A. et al., "Evidence of Mammalian Phylogeny from Sequences of Exon 28 of the von Willebrand Factor Gene," *Mol Phylogenet Evol* 5:89–101 (1996).

Read, M.S. et al., "Venom Coagglutinin for Detection of von Willebrand Factor Activity in Animal Plasmas," *J. Lab. Clin. Med.* 101:74–82 (1983).

Richards, B. et al., "Multiplex PCR Amplification from the CFTR Gene Using DNA Prepared from Buccal Bushes/Swabs," *Human Molecular Genetics* 2:159–163 (1992).

Rosborough, T.K. et al., "Measurement of Canine von Willebrand Factor Using Ristocetin and Polybrene," *J. Lab. Clin. Med.* 96:47–56 (1980).

Rudolph, J.A. et al., "Periodic Paralysis in Quarter Horses: a Sodium Channel Mutation Disseminated by Selective Breeding," *Nat. Genet.* 2:144–147 (1992).

Ruggeri, Z.M., et al., "von Willebrand Factor," *FASEB J.* 7:308–316 (1993).

Sadler, J.E. et al., "Commentary: A New Classification for von Willebrand Disease," *Blood* 84:676–679 (1994).

Sambrook J. et al., "Identification of cDNA Clones of Interest," *Molecular Cloning: A Laboratory Manual*, Second Edition, vol. 2, Cold Spring, NY at pp. 8.46–8.47 (1989).

Shibuya, H. et al., "A Polymorphic $(AGGATT)_n$ Tandem Repeat in an Intron of the Canine von Willebrand Factor Gene," *Anim. Genet* 25:122 (1994).

Shuster, D.E. et al., "Identification and Prevalence of a Genetic Defect that Causes Leukocyte Adhesion Deficiency in Holstein Cattle," *PNAS (USA)* 89:9225–9229 (1992).

Slappendel, R.J., "von Willebrand's Disease in Dutch Kooiker Dogs," *Vet–Q* 17:S21–S22 (1995).

Stirling, Y. et al., "Heamostasis in Normal Pregnancy," *Thromb Haemostasis* 52:176–182 (1984).

Stokol, T. et al., "Stability of von Willebrand Factor and Factor VIII in Canine Cryopecipitate Under Various Conditions of Storage," *Res. Vet. Sci.* 59:152–155 (1995).

Strauss, H.S. et al., "Elevation of Factor VIII (Antihemophilic Factor) During pregnancy in Normal Persons and in a Patient with von Willebrand's Disease," *New Eng. J. Med.* 269:1251–1252 (1963).

Turrentine, M.A., et al., "Plasma from Donor Dogs, Pretreated with DDAVP, Tranfused into a German Shorthair Pointer with Type II von Willebrand's Disease," *Vet. Clin. North Am. Small Anim. Pract* 18:275 (1988).

Venta, P.J. et al., "Gene–Specific Universal Mammalian Sequence–Tagged Sites: Application to the Canine Genome" *Biochem. Genet.* 34:321–341 (1996).

Verweij, C,L. et al., Expression of Variant von Willebrand Factor (vWF) cDNA in heterologous Cells: Requirement of the Pro–polypeptide in vWF Multimer Formation,: *EMBO J.* 6:2885–2890 (1987).

Wise, R.J. et al., "The Propeptide of von Willebrand Factor Independently Mediates the Assembly of von Willebrand Multimers," *Cell* 52:229–236 (1988).

Eikenboom, J.C.J. et al., "Dominant Type 1 von Willebrand Disease Caused by Mutated Cysteine Residues in the D3 Domain of von Willebrand Factor," *Blood* 88:(7)2433–2441 (1996).

Holmes, N.G. et al., "Von Willebrand's disease in UK dobermanns: Possible correlation of a polymorphic DNA marker with disease status," *J. Small An. Prac* 37:307–308 (1996).

Johnson et al., "Canine von Willebrand's Disease: A Hetergenous Group Of Bleeding Disorders," *Vet. Clin. North Am. Small Anim. Pract.* 18:195–229 (1988).

Krawcsak, M. et al., "The mutational spectrum of single base–pair substitutions in mRNA splice junctions of human genes: causes and consequences," *Genet.* 90:41–54 (1992).

Maquat, L.E., "Defects in RNA Splicing and the Consequence of Shortened Translational Reading Frames," *Am J Hum Genet* 59:279–286 (1996).

Meinkoth, J.H. et al., "Measurement of von Willebrand factor–specific mRNA and release and storage of von Willebrand factor from endothelial cells of dogs with type–I von Willebrand's disease," *Am. J. Vet. Res.* 56(12):1577–1585 (1995).

Moser et al., "Temporal variation and factors affecting measurment of canine von Willebrand factor," *Am. J. Vet. Res.* 57:1288–1293 (1996).

Nakai, K. et al., "Construction of a novel database containing aberrant splicing mutations of mammalian genes," *Gene* 141:171–177 (1994).

Nichols, W.C. et al., "von Willebrand Disease in the RIIIS/J Mouse Is Caused By A Defect Outside of the von Willebrand Factor Gene," *Blood* 83:3225–3231 (1994).

Shapiro, M.B. et al., "RNA splice junctions of different classes of eukaryotes: sequence statistics and functional implications in gene expression," *Nucleic Acids Res.* 15(17):7155–7175 (1987).

Siguret, V. et al., "A novel case of compound heterozygosity with "Normandy"/type I von Willebrand disease (vWD). Direct demonstration of the segregation of one allele with a defective expression at the mRNA level causing type I vWD," *Hum. Genet.* 93:95–102 (1994).

Stokol et al., "von Willebrand's disease in Dobermann dogs in Australia," *Aust. Vet. J.* 72:257–262 (1996).

```
   1  CATTAANAGG  TCCTGGCTGG  GAGCTTTTTT  TTGGGACCAG  CACTCCATGT  TCAAGGGCAA
  61  ACAGGGGCCA  ATTAGGATCA  ATCTTTTTTC  TTTCTTTTTT  TAAAAAAAAA  AATTCTTCCC
 121  ACTTTGCACA  CGGACAGTAG  TACATACCAG  TAGCTCTCTG  CGAGGACGGT  GATCACTAAT
 181  CATTTCTCCT  GCTTCGTGGC  AGATGAGTCC  TACCAGACTT  GTGAGGGTGC  TGCTGGCTCT
 241  GCCCTCATC   TTGCCAGGGA  AACTTTGTAC  AAAAGGGACT  GTTGGAAGGT  CATCGATGGC
 301  CCGATGTAGC  CTTCTCGGAG  GTGACTTCAT  CAACACCTTT  GATGAGAGCA  TGTACAGCTT
 361  TGCGGGAGAT  TGCAGTTACC  TCCTGGCTGG  GGACTGCCAG  GAACACTCCA  TCTCACTTAT
 421  CGGGGGTTTC  CAAAATGACA  AAAGAGTGAG  CCTCTCCGTG  TATCTCGGAG  AATTTTTCGA
 481  CATTCATTTG  TTTGTCAATG  GTACCATGCT  GCAGGGGACC  CAAAGCATCT  CCATGCCCTA
 541  CGCCTCCAAT  GGGCTGTATC  TAGAGGCCGA  GGCTGGCTAC  TACAAGCTGT  CCAGTGAGGC
 601  CTACGGCTTT  GTGGCCAGAA  TTGATGGCAA  TGGCAACTTT  CAAGTCCTGC  TGTCAGACAG
 661  ATACTTCAAC  AAGACCTGTG  GGCTGTGTGG  CAACTTTAAT  ATCTTTGCTG  AGGATGACTT
 721  CAAGACTCAA  GAAGGGACGT  TGACTTCGGA  CCCCTATGAC  TTTGCCAACT  CCTGGCCCT
 781  GAGCAGTGGG  GAACAACGGT  GCAAACGGGT  GTCCCCTCCC  AGCAGCCCAT  GCAATGTCTC
 841  CTCTGATGAA  GTGCAGCAGG  TCCTGTGGGA  GCAGTGCCAG  CTCCTGAAGA  GTGCCTCGGT
 901  GTTTGCCCGC  TGCCACCCGC  TGGTGGACCC  TGAGCCTTTT  GTCGCCCTGT  GTGAAAGGAC
 961  TCTGTGCACC  TGTGTCCAGG  GGATGGAGTG  CCCTTGTGCG  GTCCTCCTGG  AGTACGCCCG
1021  GGCCTGTGCC  CAGCAGGGGA  TTGTCTTGTA  CGGCTGGACC  GACCACAGCG  TCTGCCGACC
1081  AGCATGCCCT  GCTGGCATGG  AGTACAAGGA  GTGCGTGTCC  CCTTGCACCA  GAACTTGCCA
1141  GAGCCTTCAT  GTCAAAGAAG  TGTGTCAGGA  GCAATGTGTA  GATGGCTGCA  GCTGCCCCGA
1201  GGGCCAGCTC  CTGGATGAAG  GCCACTGCGT  GGGAAGTGCT  GGGAAGTTCT  GTGTGCATGC
1261  TGGGCAACGG  TACCCTCCGG  GCGCCTCCCT  CTTACAGGAC  TGCCACACCT  GCATTTGCCG
1321  AAATAGCCTG  TGGATCTGCA  GCAATGAAGA  ATGCCCAGGC  GAGTGTCTGG  TCACAGGACA
1381  GTCCCACTTC  AAGAGCTTCG  ACAACAGTA   CTTCACCTTC  AGTGGGGTCT  GCCACTACCT
1441  GCTGGCCCAG  GACTGCCAGG  ACCACACATT  CTCTGTTGTC  ATAGAGACTG  TCCAGTGTGC
1501  CGATGACCTG  GATGCTGTCT  GCACCCGCTC  GGTCACCGTC  CGCCTGCCTG  GACATCACAA
```

*FIG. 1A*

```
1561 CAGCCTTGTG AAGCTGAAGA ATGGGGGAGG AGTCTCCATG GATGGCCAGG ATATCCAGAT
1621 TCCTCTCCTG CAAGGTGACC TCCGCATCCA GCACACCGTG ATGGCCTCCG TGCGCCTCAG
1681 CTACGGGGAG GACCTGCAGA TGGATTCGGA CGTCCGGGGC AGGCTACTGG TGACGCTGTA
1741 CCCCGCCTAC GCGGGGAAGA CGTGCGGCCG TGGCGGGAAC TACAACGGCA ACCGGGGGA
1801 CGACTTCGTG ACGCCCGCA GCCTGGCGGA GCCCCTGGTG GAGGACTTCG GGAACGCCTG
1861 GAAGCTGCTC GGGGCCTGCG AGAACCTGCA GAAGCAGCAC CGCGATCCCT GCAGCCTCAA
1921 CCCGCGCCAG GCCAGGTTTG CGGAGGAGGC GTGCCGCGCTG CTGACGTCCT CGAAGTTCGA
1981 GCCCTGCCAC CGAGCGGTGG GTCCCTCAGC CTACGTGCAG AACTGCCTCT ACGACGTCTG
2041 CTCCTGCTCC GACGGCAGAG CAGCGCCCGTG GGAGCCGGC CCCAACTACG CCGCAGCCGT
2101 GGCCCGGAGG GGCGTGCACA TCGCGTGGCG GGAGCCGGC TTCTGTGCGC TGAGCTGCCC
2161 CCAGGGCCAG GTGTACCTGC AGTGTGGGAC CCCCTGCAAC ATGACCTGTC TCTCCCTCTC
2221 TTACCCGGAG GAGGACTGCA ATGAGGTCTG CTTGGAAAGC TGCTTCTCCC CCCAGGGCT
2281 GTACCTGGAT GAGAGGGGAG ATTGTGTGCC CAAGGCTCAG TGTCCCTGTT ACTATGATGG
2341 TGAGATCTTT CAGCCCCGAAG ACATCTTCTC AGACCATCAC ACCATGTGCT ACTGTGAGGA
2401 TGGCTTCATG CACTGTACCA CAAGTGGAGG CCTGGGAAGC GAGCCCTGTCC ACCCGGTGCT
2461 CAGCAGCCCC CGGTGTGTCA CC GCAGCAAAAG GCAGCTGTGCCA CCATGGTCAA
2521 GTTGGTGTGT CCCGCTGATA ACCCGAGGGC TGAAGGACTG GAGTGTGCCA AAACCTGCCA
2581 GAACTATGAC CTGCAGTGCA TGTGTCTCTCC GGCTGCCTCT GCCCGCCAGG
2641 CATGGTCCGG CATGAAAACA GGTGTGTGGC GCTGGAAAGA TGTCCCTGCT TCCACCAAGG
2701 CCAAGAGTAC GCCCCAGGAG AAACCGTGAA AATTGACTGC AACACTTGTG TCTGTCGGA
2761 CCGGAAGTGG ACCTGCACAG ACCATGTGTG TGATGCCCACT TGCTCTGCCA TCGGCATGCC
2821 GCACTACCTC ACCTTCGACG GACTCAAGTA CCTGTTCCCT GGGAGTGCC AGTATGTCT
2881 GGTGCAGGAT TACTGCGGCA GTAACCCTGG GACCTTACGG ATCCTGGTGG GGAACGAGGG
2941 GTGCAGCTAC CCCTCAGTGA AATGCAAGAA GCGGGTCACC ATCCTGGTGG AAGGAGAGA
3001 GATTGAACTG TTTGATGGG AGGTGAATGT GAAGAAACCC ATGAAGGATG AGACTCACTT
3061 TGAGGTGGTA GAGTCTGGTC AGTACGTCAT TCTGCTGCTG GGCAAGGCAC TCTCTGTGGT
3121 CTGGGACCAC CGCCTGAGCA TCTCTGTGCA CCTGAAGCGG ACATACCAGG AGCAGGTGTG
```

*FIG. 1B*

```
3181  TGGCCTGTGT  GGGAATTTTG  ATGGCATCCA  GAACAATGAT  TTCACCAGCA  GCAGCCTCCA
3241  AATAGAAGAA  GACCCTGTGG  ACTTTGGGAA  TTCCTGGAAA  GTGAACCCGC  AGTGTGCCGA
3301  CACCAAGAAA  GTACCACTGG  ACTCATCCCC  TGCCGTCTGC  CACAACAACA  TCATGAAGCA
3361  GACGATGGTG  GATTCCTCCT  GCAGGATCCT  CACCAGTGAT  ATTTTCCAGG  ACTGCAACAG
3421  GCTGGTGGAC  CCTGAGCCAT  TCCTGGACAT  TTGCATCTAC  GACACTTGCT  CCTGTGAGTC
3481  CATTGGGGAC  TGCACCTGCT  TCTGTGACAT  CATTGCTGCT  TACGCCCACG  TCTGTGCCCA
3541  GCATGGCAAG  GTGGTAGCCT  GGAGGACAGC  CACATTCTGT  CCCCAGAATT  GCGAGGAGCG
3601  GAATCTCCAC  GAGAATGGGT  ATGAGTGTGA  GTGGCGCTAT  AACAGCTGTG  CCCCTGCCTG
3661  TCCCAGCACG  TGCCAGCACC  CCGAGCCACT  GGCATGCCCT  GTACAGTGTG  TTGAAGGTTG
3721  CCATGCGCAC  TGCCCCTCCA  GGAAAATCCT  GGATGAGCTT  TTGCAGACCT  GCATCGACCC
3781  TGAAGACTGT  CCTGTGTGTG  AGGTGGCTGG  TCGTCGCTTG  GCCCCAGGAA  AGAAAATCAT
3841  CTTGAACCCC  AGTGACCCTG  TGCACACTGCA  AATTTGTAAT  TGTGATGGTG  TCAACTTCAC
3901  CTGTAAGGCC  TGCAGAGAAC  CCGGAAGTGT  GGAGCCGCCC  CCCACAGATG  GCCCCATTGG
3961  CTCTACCACC  TCGTATGTGG  AGGACACGTC  CTCCATGACT  TCCACTGCAG
4021  CAGGCTTCTG  GACCTGGTTT  TCCTGCTGGA  TGGCTCCTCC  AAGCTGTCTG  AGGACGAGTT
4081  TGAAGTGCTG  AAGGTCTTTG  TGTGGGTAT   GATGGAGCAT  CTGCACATCT  CCCAGAAGCG
4141  GATCCGCGTG  GCTGTGGTGG  AGTACCACGA  CGGCTCCCAC  GCCTACATCG  AGCTCAAGGA
4201  CCGGAAGCGA  CCCTCAGAGC  TGCGGCGCAT  CGGAAGTACG  GTGAAGTACG  CGGGCAGCGA
4261  GGTGGCCTCC  ACCAGTGAGG  TCTTAAAGTA  CACGCTGTTC  CAGATCTTTG  GCAAGATCGA
4321  CCGCCCGGAA  GCGTCTCGCA  TTGCCCTGCT  CCTGATGGCC  AGCCAGGAGC  CCTCAAGGCT
4381  GGCCCGGAAT  ATGTGCAGGG  CCTGAAGAAG  AAGAAAGTCA  TTGTCATCCC
4441  TGTGGGCATC  GGGCCCCACG  CCAGCCTTAA  GCAGATCCAC  CTCATAGAGA  AGCAGGCCCC
4501  TGAGAACAAG  GCCTTTGTGT  TCAGTGGTGT  GGATGAGTTG  GAGCAGCGAA  GGGATGAGAT
4561  TATCAACTAC  CTCTGTGACC  TTGCCCCCGA  AGCACCTGCC  CCTACTCAGC  ACCCCCAAT
4621  GGCCCAGGTC  ACGGTGGGTT  CGGAGCTGTT  GGGGGTTTCA  TCTCCAGGAC  CCAAAGGAA
4681  CTCCATGGTC  CTGGATGTGG  TGTTTGTCCT  GGAAGGGTCA  GACAAAATTG  GTGAGGCCAA
4741  CTTTAACAAA  AGCAGGGAGT  TCATGGAGGA  GGTGATTCAG  CGGATGGACG  TGGGCCAGGA
```

```
4801  CAGGATCCAC GTCACAGTGC TGCAGTACTC GTACATGGTG ACCGTGGAGT ACACCTTCAG
4861  CGAGGCGCAG TCCAAGGGCG AGGTCCTACA GCAGGTGCGG GATATCCGAT ACCGGGGTGG
4921  CAACAGGACC AACACTGGAC TGGCCCCTGCA ATACCTGTCC GAACACAGCT TCTCGGTCAG
4981  CCAGGGGGAC CGGGAGCAGG TACCTAACCT GGTCTACATG GTCACAGGAA ACCCCGCTTC
5041  TGATGAGATC AAGCGGATGC CTGGAGACAT CCAGGTGGTG CCCATCGGGG TGGGTCCACA
5101  TGCCAATGTG CAGGAGCTGG AGAAGATTGG CTGCCCCAAT GCCCCCATCC TCATCCATGA
5161  CTTTGAGATG CTCCCTCGAG AGGCTCCTGA TCTGGTGCTA CAGAGGTGCT GCTCTGGAGA
5221  GGGGCTGCAG ATCCCCACCC TCTCCCCCAC CCCAGATTGC AGCCAGCCCC TGGATGTGGT
5281  CCTCCTCCTG GATGGCTCTT CCAGCATTCC AGCTTCTTAC TTTGATGAAA TGAAGAGCTT
5341  CACCAAGGCT TTTATTTCAA GAGCTAATAT AGGGCCCCCGG CTCACTCAAG TGTCGGTGCT
5401  GCAATATGGA AGCATCACCA CTATCGATGT GCCTTGGAAT GTAGCCTATG AGAAAGTCCA
5461  TTTACTGAGC CTTGTGGACC TCATGCAGCA GGAGGGAGGC CCCAGCAGGC TTGGGGATGC
5521  TTTGAGCTTT GCCGTGCGAT ATGTCACCTC AGAAGTCCAT GGTGCCAGGC CCGAGCCCTC
5581  GAAAGCGGTG GTTATCCTAG TCACAGATGT CTCCGTGGAT TCAGTGGATG CTGCAGCCGA
5641  GGCCGCCAGA TCCAACCGAG TGACAGTGTT CCCCATTGGA ATCGGGGATC GGTACAGTGA
5701  GGCCCAGCTG AGCAGCTTGG CAGGCCCAAA GGCTGGCTCC AATATGGTAA GGCTCCAGCG
5761  AATTGAAGAC CTCCCCACCG TGGCCCACCCT GGGAAATTCC TTCTTCCACA AGCTGTGCTC
5821  TGGGTTTGAT AGAGTTTGCG TGGATGAGGA TGGGAATGAG AAGAGGCCCG GGGATGTCTG
5881  GACCTTGCCA GACCAGTGCC ACACAGTGAC TTGCCTGCCA GATGGCCAGA CCTTGCTGAA
5941  GAGTCATCGG GTCAACTGTG ACCGGGGGCC AAGGCCTTCG TGCCCCAATG GCCAGCCCCC
6001  TCTCAGGGTA GAGGAGACCT GTGGCTGCCG CTGGACCTGT CCCTGTGTGT GCATGGGCAG
6061  CTCTACCCGG CACATCGTGA CCTTTGATGG GCAGAATTTC AAGCTGACTG GCAGCTGTTC
6121  GTATGTCCTA TTTCAAAACA AGGAGCAGGA CCTGGAGGTG ATTCTCCAGA ATGGTGCCTG
6181  CAGCCCTGGG GCGAAGGAGA CCTGCATGAA ATCCATTGAG GTGAAGCATG ACGGCCTCTC
6241  AGTTGAGCTC CACAGTGACA TGCAGATGAC AGTGAATGGG AGACTAGTCT CCATCCCATA
6301  TGTGGGTGGA GACATGGAAG TCAATGTTTA TGGGACCATC ATGTATGAGG TCAGATTCAA
6361  CCATCTTGGC CACATCTTCA CATTCACCCC CCAAAACAAT GAGTTCCAGC TGCAGCTCAG
```

| | | | | | |
|---|---|---|---|---|---|
| 6421 | CCCAGGACC | TTTGCTTCGA | AGACATATGG | TCTCTGTGGG | ATCTGTGATG | AGAACGGAGC |
| 6481 | CAATGACTTC | ATTCTGAGGG | ATGGGACAGT | CACCACAGAC | TGGAAGGCAC | TCATCCAGGA |
| 6541 | ATGGACCGTA | CAGCAGCTTG | GGAAGACATC | CCAGCCTGTC | CATGAGGAGC | AGTGTCCTGT |
| 6601 | CTCCGAATTC | TTCCACTGCC | AGGTCCTCCT | CTCAGAATTG | TTTGCCGAGT | GCCACAAGGT |
| 6661 | CCTCGCTCCA | GCCACCTTTT | ATGCCATGTG | CCAGCCCGAC | AGTTGCCACC | CGAAGAAAGT |
| 6721 | GTGTGAGGCG | ATTGCCTTGT | ATGCCCACCT | CTGTCGGACC | AAAGGGGTCT | GTGTGGACTG |
| 6781 | GAGGAGGGCC | AATTTCTGTG | CTATGTCATG | TCCACCATCC | CTGGTGTACA | ACCACTGTGA |
| 6841 | GCATGGCTGC | CCTCGGCTCT | GTGAAGGCAA | TACAAGCTCC | TGTGGGGACC | AACCCTCGGA |
| 6901 | AGGCTGCTTC | TGCCCCCCAA | ACCAAGTCAT | GCTGGAAGGT | AGCTGTGTCC | CCGAGGAGGC |
| 6961 | CTGTACCCAG | TGCATCAGCG | AGGATGGAGT | CCGCACCAG | TTCCTGGAAA | CCTGGGTCCC |
| 7021 | AGCCCACCAG | CCTTGCCAGA | TCTGCACGTG | CCCTCAGTGGG | CGGAAGGTCA | ACTGTACGTT |
| 7081 | GCAGCCCTGC | CCCACAGCCA | AAGCTCCCAC | CTGTGGCCCG | TGTGAAGTGG | CCCGCCTCCG |
| 7141 | CCAGAACGCA | GTGCAGTGCT | GCCCGGAGTA | CGAGTGTGTG | TGTGACCTGG | TGAGCTGTGA |
| 7201 | CCTGCCCCCG | GTGCCTCCCT | GCCGAAGATGG | CCTCCAGATG | ACCCTGACCA | ATCCTGCGA |
| 7261 | GTGCAGACCC | AACTTCACCT | GTGCCTGCAG | GAAGGATGAA | TGCAGACGGG | AGTCCCGCC |
| 7321 | CTCTTGTCCC | CCGCACCGGA | CGCCGGCCCT | TCGGAAGACT | CAGTGCTGTG | ATGAGTATGA |
| 7381 | GTGTGCATGC | AACTGTGTCA | ACTCCACGT | GAGCTGCCCG | CTTGGGTACC | TGGCCTCGGC |
| 7441 | TGTCACCAAC | GACTGTGGCT | GCACCACAAC | AACCTGCTTC | CCTGACAAGG | TGTGTGTCCA |
| 7501 | CCGAGGCACC | ATCTACCCTG | TGGGCCAGTT | CTGGGAGGAG | GCCTGTGACG | TGTGCACCTG |
| 7561 | CACGGACTTG | GAGGACTCTG | TGATGGGCCT | GCGTGTGGCC | CAGTGCTCCC | AGAAGCCCTG |
| 7621 | TGAGGACAAC | TGCCTGTCAG | GCTTCACTTA | TGTCCTTCAT | GAAGGCGAGT | GCTGTGGAAG |
| 7681 | GTGTCTGCCA | TCTGCCTGTG | AGGTGGTCAC | TGGTTCACCA | CGGGCGACG | CCCAGTCTCA |
| 7741 | CTGGAAGAAT | GTTGGCTCTC | ACTGGGCCTC | CCCTGACAAC | CCCTGCCTCA | TCAATGAGTG |
| 7801 | TGTCCCAGTG | AAGGAAGAGG | TCTTTGTGCA | ACAGAGGAAT | GTCTCCTGCC | CCCAGCTGAA |
| 7861 | TGTCCCCACC | TGCCCACGG | GCTTCCAGCT | GAGCTGTAAG | ACCTCAGAGT | GTTGTCCCAC |
| 7921 | CTGTCACTGC | GAGCCCCTGG | AGGCCTGCTT | GCTCAATGGT | ACCATCATTG | GGCCGGGAAA |
| 7981 | AAGTCTCGATG | ATTGATGTGT | GTACAACCTG | CCGCTGCACC | GTGCCGGTGG | GAGTCATCTC |

*FIG. 1E*

```
8041 TGGATTCAAG CTGGAGGGCA GGAAGACCAC CTGTGAGGCA TGCCCCCTGG GTTATAAGGA
8101 AGAGAAGAAC CAAGGTGAAT GCTGTGGGAG ATGTCTGCCT ATAGCTTGCA CCATTCAGCT
8161 AAGAGGAGGA CAGATCATGA CACTGAAGCG TGATGAGACT ATCCAGGATG GCTGTGACAG
8221 TCACTTCTGC AAGGTCAATG AAAGAGGAGA GTACATCTGG GAGAAGAGAG TCACGGGTTG
8281 CCCACCTTTC GATGAACACA AGTGTCTGGC TGAGGGAGGA AAAATCATGA AAATTCCAGG
8341 CACCTGCTGT GACACATGTG AGGAGCCAGA ATGCAAGGAT ATCATTGCCA AGCTGCAGCG
8401 TGTCAAAGTG GGAGACTGTA AGTCTGAAGA GGAAGTGGAC ATTCATTACT GTGAGGGTAA
8461 ATGCCAGC AAAGCCGTGT ACTCCATCCA CATGGAGGAC GTGCAGGACC AGTGCTCCTG
8521 CTGCTCGCCC ACCCAGACGG AGCCCCATGC GGTGGCCCTG CGCTGCACCA ATGGCTCCCT
8581 CATCTACCAT GAGATCCTCA ATGCCATCGA CTGCCTTGCG TCCCCAGGA AGTGCAGCAA
8641 GTGAGGCCAC TGCCTGGATG CTACTGTCGC CTGCCTTACC CGACCTCACT GGACTGGCCA
8701 GAGTGCTGCT CAGTCCCTCCT CAGTCCCTGC CCTGCTCTGC TCTTGTGCTT CCTGATCCCA
8761 CAATAAAGGT CAATCTTTCA CCTTGAAAAA AAAAAAAAAA AA
```

*FIG. 1F*

```
Human  MIPARFAGVLLALALILPGTLCAEGTRGRSSTARCSLFGSDFVNTFDGSMYSFAGYCSYL    60
Dog    -S-T-LVR-------------K--TK--V-----M----L-G--I----E-----D---
                            *

Human  LAGGCQKRSFSIIGDFQNGKRVSLSVYLGEFFDIHLFVNGTVTQGDQRVSMPYASKGLYL   120
Dog    ---D--EH-I--L--G-----D----------------ML--T-SI------N---

Human  ETEAGYYKLSGEAYGFVARIDGSGNFQVLLSDRYFNKTCGLCGNFNIFAEDDFMTQEGTL   180
Dog    --A--------S-----N---------------------------K--

Human  TSDPYDFANSWALSSGEQWCERASPPSSSCNISSGEMQKGLWEQCQLLKSTSVFARCHPL   240
Dog    ---------------------R-K-V-----P--V--D-V-QV------A---

Human  VDPEPFVALCEKTLCECAGGLECACPALLEYARTCAQEGMVLYGWTDHSACSPVCPAGME   300
Dog    ---------R------T-VQ-M--P-AV-------A----Q--I------V-R-A---

Human  YRQCVSPCARTCQSLHINEMCQERCVDGCSCPEGQLLDEGLCVESTECPCVHSGKRYPPG   360
Dog    --KE-----T-------VK-V--Q-------------H--G-A--S----A-Q---

Human  TSLSRDCNTCICRNSQWICSNEECPGECLVTGQSHFKSFDNRYFTFSGICQYLLARDCQD   420
Dog    A---LQ--H-----L--------------------V-H----Q---

Human  HSFSIVIETVQCADDRDAVCTRSVTVRLPGLHNSLVKLKHGAGVAMDGQDVQLPLLKGDL   480
Dog    --T--V----------L---------------N-G--S----I-I---Q---

Human  RIQHTVTASVRLSYGEDLQMDWDGRGRLLVKLSPVYAGKTCGLCGNYNGNQGDDFLTPSG   540
Dog    -------M-----------S-V------T-Y-A------RG-----R-----V--A-

Human  LAEPRVEDFGNAWKLHGDCQDLQKQHSDPCALNPRMTRFSEEACAVLTSPTFEACHRAVS   600
Dog    ----L---------------L-A-EN----R---S----QA--A----L---SK--P----G
```

FIG.2A

```
Human  PLPYLRNCRYDVCSCSDGRECLCGALASYAAACAGRGVRVAWREPGRCELNCPKGQVYLQ   660
Dog    ----Q--VQ--L--------D-------S-V-N-----V-R----HI-----F-A-S--Q---

Human  CGTPCNLTCRSLSYPDEECNEACLEGCFCPPGLYMDERGDCVPKAQCPCYYDGEIFQPED   720
Dog    --------------M--L-----E-D---V----S---L-------

Human  IFSDHHTMCYCEDGFMHCTMSGVPGSLLPDAVLSSPLSHRSKRSLSCRPPMVKLVCPADN   780
Dog    ----------------------------T---GL-----NP----RC-------------

Human  LRAEGLECTKTCQNYDLECMSMGCVSGCLCPPGMVRHENRCVALERCPCFHQGKEYAPGE   840
Dog    P--------A------T-----------------Q-------------------------

Human  TVKIGCNTCVCRDRKWNCTDHVCDATCSTIGMAHYLTEDGLKYLFPGECQYVLVQDYCGS   900
Dog    ---D--------------T---------A-------------------------------

Human  NPGTFRILVGNKGCSHPSVKCKKRVTILVEGGEIELEDGEVNVKRPMKDETHFEVVESGR   960
Dog    -----L----E--Y------------------------------K-------------Q Human  YIILLLGKALSVVWDRHLSISVVLKQTYQEKVCGLCGNFDGIQNNDLTSSNLQVEEDPVD  1020
Dog    --V-----------HR------T-R---Q-------------F---S---I---------

Human  FGNSWKVSSQCADTRKVPLDSSPATCHNNIMKQTMVDSSCRILTSDVFQDCNKLVDPEPY  1080
Dog    -------NP--------K------V-----------------------I---R----F-

Human  LDVCIYDTCSCESIGDCACFCDTIAAYAHVCAQHGKVVTWRTATLCPQSCEERNLRENGY  1140
Dog    --I-----------------T------------A---F---N----H---

Human  ECEWRYNSCAPACQVTCQHPEPLACPVQCVEGCHAHCPPGKILDELLQTCVDPEDCPVCE  1200
Dog    ---------------------PI---------------------I---------------
```

*FIG. 2B*

```
Human  VAGRRFASGKKVTLNPSDPEHCQICHCDVVNLTCEACQEPGGLVVPPTDAPVSPTTLYVE   1260
Dog    -----L-P----II------------N--G--F--K--R----SV------G-IGS--S--

Human  DISEPPLHDFYCSRLLDLVFLLDGSSRLSEAEFEVLKAFVVDMMERLRISQKWVRVAVVE   1320
Dog    ---T------H--------------K--D-----V---G---H-H----RI---------

Human  YHDGSHAYIGLKDRKRPSELRRIASQVKYAGSQVASTSEVLKYTLFQIFSKIDRPEASRI   1380
Dog    ---------------E-------T------------E-----------G-----------

Human  ALLLMASQEPQRMSRNFVRYVQGLKKKVIVIPVGIGPHANLKQIRLIEKQAPENKAFVL   1440
Dog    --------------S-LA--L--------------------S-----H---------F-

Human  SSVDELEQQRDEIVSYLCDLAPEAPPTLPPHMAQVTVGPGLLGVSTLGPKRNSMVLDVA   1500
Dog    --G------R----IN---------A--QH-P---------SE-----SP--------V Human  FVLEGSDKIGEADFNRSKEFMEEVIQRMDVGQDSIHVTVLQYSYMVTVEYPFSEAQSKGD   1560
Dog    -------------N--R-----------------R-------T---------T-----E Human  ILQRVREIRYQGGNRTNTGLALRYLSDHSFLVSQGDREQAPNLVYMVTGNPASDEIKRLP   1620
Dog    V--Q---D---R----------Q---E---S-------V----------------M---

Human  GDIQVVPIGVGPNANVQELERIGWPNAPILIQDFETLPREAPDLVLQRCCSGEGLQIPTL   1680
Dog    -----------H---------K------------H--M----------------------

Human  SPAPDCSQPLDVILLLDGSSSFPASYFDEMKSFAKAFISKANIGPRLTQVSVLQYGSITT   1740
Dog    --T--------V------------I---------T----R-------------------

Human  IDVPWNVVPEKAHLLSLVDVMQREGGPSQIGDALGFAVRYLTSEMHGARPGASKAVVILV   1800
Dog    ----AY--V----------L--Q----E-----S----V----V----------------
```

*FIG. 2C*

```
Human  TDVSVDSVDAAADAARSNRVTVFPIGIGDRYDAAQLRILAGPAGDSNVVKLQRIEDLPTM  1860
Dog    ------------E---------------------------SE----SS-----KAG--M-R------V Human  VTLGNSFLHKLCSGFVRICMDEDGNEKRPGDVWTLPDQCHTVTCQPDGQTLLKTHRVNCD  1920
Dog    A--------F-------D-V-V-------------------------L------S-----

Human  RGLRPSCPNSQSPVKVEETCGCRWTCPCVCTGSSTRHIVTEDGQNFKLTGSCSYVLFQNK  1980
Dog    --P-----G-P-LR-------------------M--------------------------

Human  EQDLEVILHNGACSPGARQGCMKSIEVKHSALSVELHSDMEVTVNGRLVSVPYVGGNMEV  2040
Dog    ----------Q-------KET---------DG----------QM------I---D----

Human  NVYGAIMHEVRFNHLGHIFTFTPQNNEFQLQLSPKTFASKTYGLCGICDENGANDFMLRD  2100
Dog    ----T--Y------------------------R-------------------I------

Human  GTVTTDWKTLVQEWTVQRPGQTCQPILEEQCLVPDSSHCQVLLLPLFAECHKVLAPATFY  2160
Dog    -----------------A-I------QL-K-S--VH----P-SEFF-----SE-------

Human  AICQQDSCHQEQVCEVIASYAHLCRTNGVCVDWRTPDFCAMSCPPSLVYNHCEHGCPRHC  2220
Dog    -M---P-----PKK---A---L-----K---------RAN-------------------L Human  DGNVSSCGDHPSEGCFCPPDKVMLEGSCVPEEACTQCIGEDGVQHQFLEAWVPDHQPCQI  2280
Dog    E---T-----Q------NQ---------------------S----R----T---A----

Human  CTCLSGRKVNCTTQPCPTAKAPTCGLCEVARLRQNADQCCPEYECVCDPVSCDLPPVPHC  2340
Dog    ---------------L-----------------P------V------L------P----

Human  ERGLQPTLTNPGECRPNFTCACRKEECKRVSPPSCPPHRLPTLRKTQCCDEYECACNCVN  2400
Dog    -D---M--------------D-R-E-------------T-A-------------------
```

| | | |
|---|---|---|
| Human | STVSCPLGYLASTATNDCGCTTTTCLPDKVCVHRSTIYPVGQFWEEGCDVCTCTDMEDAV | 2460 |
| Dog | ------------AV-----------F-------G------A-------L--S | |
| Human | MGLRVAQCSQKPCEDSCRSGFTYVLHEGECCGRCLPSACEVTGSP[RGD]SQSSWKSVGSQ | 2520 |
| Dog | --------------N-L----------------------[A--]-H--N---H | |
| Human | WASPENPCLINECVRKEEVFIQQRNVSCPQLEVPVCPSGFQLSCKTSACCPSCRCERME | 2580 |
| Dog | ------D-----------------V------N-T--T-----E--T-H--PL- | |
| Human | ACMLNGTVIGPGKTVMIDVCTTCRCMVQVGVISGFKLECRKTTCNPCPLGYKEENNTGEC | 2640 |
| Dog | ----L---I-----SL---------T-P--------G----EA--K-Q-- | |
| Human | CGRCLPTACTIQLRGGQIMTLKRDETLQDGCDTHFCKVNERGEYFWEKRVTGCPPFDEHK | 2700 |
| Dog | --------I-----------------S-------I---------- | |
| Human | CLAEGGKIMKIPGTCCDTCEEPECNDITARLQYVKVGSCKSEVEVDIHYCQGKCASKAMY | 2760 |
| Dog | --------------------K--I-K--R---D----E-----V----- | |
| Human | SIDINDVQDQCSCCSPTRTEPMQVALHCTNGSVVYHEVLNAMECKCSPRKCSK | 2813 |
| Dog | --HME---------Q--------R----LI---I---R---- | | exon 4    AAATGACAAAAGAGTGAGCCGGTC*
AGGGGGTTTCCAAAATGACAAAAGAGTGAGCCTCCGTGTATCTCCGAGAATTTTCGA
 G  G  F  Q  N  D  K  R  V  S  L  S  V  Y  L  G  E  F  F  D CATTCATTGTTTGTCAATGGTACCATGCTGCAGGGACCCAAAGTAAGTCAGAAGCCC
 I  H  L  F  V  N  G  T  M  L  Q  G  T  Q  R

GAATGTTCAGGTTAATATGGACCCCTGGGGATCACTTTGCAACCCCCTGTTTTTCAGAT

GAGGGAGCCGGGGCCCAGAGACAGGAAGTAAATGTGCCCAGGGAAAGTGAGTGGCAGGAC

TGGGTGAAAGCCCCATATCCCGACTCCCTGGTCAAGGAGACTTTGCACCAAGGTCCCAGCC
                      3'-GGGCTGGCGACCAGTTCCTCTGAA-5'

CTGGAGCATGGGGGTTGGGAAGGTGGAGGACATGGAGGAGGAAATGCATGAGAAGCAC exon 5
GCTTCCTGAGCTCCCTTGTCCCACCAGCATCTCCATGCCCTACGCCTCCAATGGGC
                           I  S  M  P  Y  A  S  N  G

*FIG. 4*

Normal Allele

```
Exon 43                Intron 43        Exon 44
                          *
AGGACAACTGCCCTGCCCTGTCGgtgagtgggg .... GGCTTCACTTAT
                       ||||||
                       AGGTRAGT  Donor Consensus
```

Mutant Allele

```
                          *
AGGACAACTGCCCTGCCCTGCCTgtcagtgagtgggg .... GGCTTCACTTAT
                       || |||
                       AGGTRAGT  Donor Consensus
```

*FIG. 6*

Exon 7

```
       V   L   W   E   Q   C   Q   L   L   K   S   A   S   V   F   A   R   C   H   P   L   V
       GTCCTGTGGGAGCAGTGCCAGCTCCTGAAGAGTGCCTCGGTGTTTGCCCGCTGCCACCCGCTGGTG
       TCCTGTGGGAGCAGTGCCAG
DVWFEX7D  GCNNNNNNNGC    Mwo I

D   P   E   P   F   V   A   L   C   E   R   T   L   C   T   C   V   Q   G   M   E   C
       GACCCTGAGCCTTTTGTCGCCCTGTGTGAAAGGACTCTGTGCACCTGTGTCCAGGGGATGGAGTGC
                               GCNNNN-NNNGC    Mwo I
                                  Δ735

P   C   A   V   L   E   Y   A   R   A   C   A   Q   Q   G   I   V   L   Y   G   W
       CCTTGTGCCGTCCTCCTGGAGTACGCCCGGGCCTGTGCCCAGCAGGGAATTGTGCTGTACGGCTGG
                                                                        ATGCCGACC

T   D   H   S   V   C   R
       ACCGACCACAGCGTCTGCCG
       TGGCTGGTG-5'
DVWFEX7U
```

FIG. 11

SEQUENCE LISTING

<160> NUMBER OF SEQ ID NOS: 29

<210> SEQ ID NO 1
<211> LENGTH: 8802
<212> TYPE: DNA
<213> ORGANISM: Canis familiaris

<400> SEQUENCE: 1
cattaaaagg tcctggctgg gagctttttt ttgggaccag cactccatgt tcaagggcaa      60

-continued

| | |
|---|---|
| acaggggcca attaggatca atcttttttc tttcttttt taaaaaaaaa aattcttccc | 120 |
| actttgcaca cggacagtag tacataccag tagctctctg cgaggacggt gatcactaat | 180 |
| catttctcct gcttcgtggc agatgagtcc taccagactt gtgagggtgc tgctggctct | 240 |
| ggccctcatc ttgccaggga aactttgtac aaaagggact gttggaaggt catcgatggc | 300 |
| ccgatgtagc cttctcggag gtgacttcat caacaccttt gatgagagca tgtacagctt | 360 |
| tgcgggagat tgcagttacc tcctggctgg ggactgccag aacactcca tctcacttat | 420 |
| cgggggtttc caaaatgaca aaagagtgag cctctccgtg tatctcggag aatttttcga | 480 |
| cattcatttg tttgtcaatg gtaccatgct gcaggggacc caaagcatct ccatgcccta | 540 |
| cgcctccaat gggctgtatc tagaggccga ggctggctac tacaagctgt ccagtgaggc | 600 |
| ctacggcttt gtggccagaa ttgatggcaa tgcaacttt caagtcctgc tgtcagacag | 660 |
| atacttcaac aagacctgtg ggctgtgtgg caactttaat atctttgctg aggatgactt | 720 |
| caagactcaa gaagggacgt tgacttcgga ccctatgac tttgccaact cctgggccct | 780 |
| gagcagtggg gaacaacggt gcaaacgggt gtcccctccc agcagcccat gcaatgtctc | 840 |
| ctctgatgaa gtgcagcagg tcctgtggga gcagtgccag ctcctgaaga gtgcctcggt | 900 |
| gtttgcccgc tgccacccgc tggtggaccc tgagcctttt gtcgccctgt gtgaaaggac | 960 |
| tctgtgcacc tgtgtccagg ggatggagtg cccttgtgcg gtcctcctgg agtacgcccg | 1020 |
| ggcctgtgcc cagcagggga ttgtcttgta cggctggacc gaccacagcg tctgccgacc | 1080 |
| agcatgccct gctggcatgg agtacaagga gtgcgtgtcc ccttgcacca gaacttgcca | 1140 |
| gagccttcat gtcaaagaag tgtgtcagga gcaatgtgta gatggctgca gctgcccga | 1200 |
| gggccagctc ctggatgaag gccactgcgt gggaagtgct gagtgttcct gtgtgcatgc | 1260 |
| tgggcaacgg taccctccgg gcgcctccct cttacaggac tgccacacct gcatttgccg | 1320 |
| aaatagcctg tggatctgca gcaatgaaga atgcccaggc gagtgtctgg tcacaggaca | 1380 |
| gtcccacttc aagagcttcg acaacaggta cttcaccttc agtggggtct gccactacct | 1440 |
| gctggcccag gactgccagg accacacatt ctctgttgtc atagagactg tccagtgtgc | 1500 |
| cgatgacctg gatgctgtct gcacccgctc ggtcaccgtc cgcctgcctg acatcacaa | 1560 |
| cagccttgtg aagctgaaga atggggagg agtctccatg gatggccagg atatccagat | 1620 |
| tcctctcctg caaggtgacc tccgcatcca gcacaccgtg atggcctccg tgcgcctcag | 1680 |
| ctacggggag gacctgcaga tggattcgga cgtccggggc aggctactgg tgacgctgta | 1740 |
| ccccgcctac gcggggaaga cgtgcggccg tggcgggaac tacaacggca accgggggga | 1800 |
| cgacttcgtg acgcccgcag gcctggcgga gcccctggtg gaggacttcg ggaacgcctg | 1860 |
| gaagctgctc ggggcctgcg agaacctgca gaagcagcac cgcgatccct gcagcctcaa | 1920 |
| cccgcgccag gccaggtttg cggaggaggc gtgcgcgctg ctgacgtcct cgaagttcga | 1980 |
| gccctgccac cgagcggtgg gtcctcagcc ctacgtgcag aactgcctct acgacgtctg | 2040 |
| ctcctgctcc gacggcagag actgtctttg cagcgccgtg ccaactacg ccgcagccgt | 2100 |
| ggcccggagg ggcgtgcaca tcgcgtggcg ggagccgggc ttctgtgcgc tgagctgccc | 2160 |
| ccagggccag gtgtacctgc agtgtgggac ccctgcaac atgacctgtc tctccctctc | 2220 |
| ttacccggag gaggactgca atgaggtctg cttggaaagc tgcttctccc cccagggct | 2280 |
| gtacctggat gagaggggag attgtgtgcc caaggctcag tgtcccctgtt actatgatgg | 2340 |
| tgagatcttt cagcccgaag acatcttctc agaccatcac accatgtgct actgtgagga | 2400 |
| tggcttcatg cactgtacca caagtggagg cctgggaagc ctgctgccca acccggtgct | 2460 |

-continued

```
cagcagcccc cggtgtcacc gcagcaaaag gagcctgtcc tgtcggcccc ccatggtcaa    2520
gttggtgtgt cccgctgata acccgagggc tgaaggactg gagtgtgcca aaacctgcca    2580
gaactatgac ctgcagtgca tgagcacagg ctgtgtctcc ggctgcctct gcccgcaggg    2640
catggtccgg catgaaaaca ggtgtgtggc gctggaaaga tgtccctgct tccaccaagg    2700
ccaagagtac gccccaggag aaaccgtgaa aattgactgc aacacttgtg tctgtcggga    2760
ccggaagtgg acctgcacag accatgtgtg tgatgccact tgctctgcca tcggcatggc    2820
gcactacctc accttcgacg gactcaagta cctgttccct ggggagtgcc agtatgttct    2880
ggtgcaggat tactgcggca gtaaccctgg gaccttacgg atcctggtgg ggaacgaggg    2940
gtgcagctac ccctcagtga aatgcaagaa gcgggtcacc atcctggtgg aaggaggaga    3000
gattgaactg tttgatgggg aggtgaatgt gaagaaaccc atgaaggatg agactcactt    3060
tgaggtggta gagtctggtc agtacgtcat tctgctgctg ggcaaggcac tctctgtggt    3120
ctgggaccac cgcctgagca tctctgtgac cctgaagcgg acataccagg agcaggtgtg    3180
tggcctgtgt gggaattttg atggcatcca gaacaatgat ttcaccagca gcagcctcca    3240
aatagaagaa gaccctgtgg actttgggaa ttcctggaaa gtgaacccgc agtgtgccga    3300
caccaagaaa gtaccactgg actcatcccc tgccgtctgc cacaacaaca tcatgaagca    3360
gacgatggtg gattcctcct gcaggatcct caccagtgat attttccagg actgcaacag    3420
gctggtggac cctgagccat tcctggacat ttgcatctac gacacttgct cctgtgagtc    3480
cattggggac tgcacctgct tctgtgacac cattgctgct tacgcccacg tctgtgccca    3540
gcatggcaag gtggtagcct ggaggacagc cacattctgt ccccagaatt gcgaggagcg    3600
gaatctccac gagaatgggt atgagtgtga gtggcgctat aacagctgtg cccctgcctg    3660
tcccatcacg tgccagcacc ccgagccact ggcatgccct gtacagtgtg ttgaaggttg    3720
ccatgcgcac tgccctccag ggaaaatcct ggatgagctt ttgcagacct gcatcgaccc    3780
tgaagactgt cctgtgtgtg aggtggctgg tcgtcgcttg gccccaggaa agaaaatcat    3840
cttgaacccc agtgaccctg agcactgcca aatttgtaat tgtgatggtg tcaacttcac    3900
ctgtaaggcc tgcagagaac ccggaagtgt tgtggtgccc ccacagatg gccccattgg    3960 ctctaccacc tcgtatgtgg aggacacgtc ggagccgccc ctccatgact ccactgcag    4020 caggcttctg gacctggttt tcctgctgga tggctcctcc aagctgtctg aggacgagtt    4080
tgaagtgctg aaggtctttg tggtgggtat gatggagcat ctgcacatct cccagaagcg    4140
gatccgcgtg gctgtggtgg agtaccacga cggctcccac gcctacatcg agctcaagga    4200
ccggaagcga ccctcagagc tgcggcgcat caccagccag gtgaagtacg cgggcagcga    4260
ggtggcctcc accagtgagg tcttaaagta cacgctgttc cagatctttg gcaagatcga    4320
ccgcccggaa gcgtctcgca ttgccctgct cctgatggcc agccaggagc cctcaaggct    4380
ggcccggaat ttggtccgct atgtgcaggg cctgaagaag aagaaagtca ttgtcatccc    4440
tgtgggcatc gggccccacg ccagccttaa gcagatccac ctcatagaga agcaggcccc    4500
tgagaacaag gcctttgtgt tcagtggtgt ggatgagttg gagcagcgaa gggatgagat    4560
tatcaactac ctctgtgacc ttgccccga agcacctgcc cctactcagc acccccaat    4620 ggcccaggtc acggtgggtt cggagctgtt ggggtttca tctccaggac ccaaaaggaa    4680
ctccatggtc ctggatgtgg tgtttgtcct ggaagggtca gacaaaattg gtgaggcaa    4740 ctttaacaaa agcagggagt tcatggagga ggtgattcag cggatggacg tgggccagga    4800
```

-continued

```
caggatccac gtcacagtgc tgcagtactc gtacatggtg accgtggagt acaccttcag   4860
cgaggcgcag tccaagggcg aggtcctaca gcaggtgcgg gatatccgat accggggtgg   4920
caacaggacc aacactggac tggccctgca atacctgtcc gaacacagct tctcggtcag   4980 ccaggggac cgggagcagg tacctaacct ggtctacatg gtcacaggaa accccgcttc    5040
tgatgagatc aagcggatgc ctggagacat ccaggtggtg cccatcgggg tgggtccaca   5100
tgccaatgtg caggagctgg agaagattgg ctggcccaat gccccatcc tcatccatga    5160 ctttgagatg ctccctcgag aggctcctga tctggtgcta cagaggtgct gctctggaga   5220
ggggctgcag atccccaccc tctcccccac cccagattgc agccagcccc tggatgtggt   5280
cctcctcctg gatggctctt ccagcattcc agcttcttac tttgatgaaa tgaagagctt   5340
caccaaggct tttatttcaa gagctaatat agggcccgg ctcactcaag tgtcggtgct    5400
gcaatatgga agcatcacca ctatcgatgt gccttggaat gtagcctatg agaaagtcca   5460
tttactgagc cttgtggacc tcatgcagca ggagggaggc cccagcgaaa ttggggatgc   5520
tttgagcttt gccgtgcgat atgtcacctc agaagtccat ggtgccaggc ccggagcctc   5580
gaaagcggtg gttatcctag tcacagatgt ctccgtggat tcagtggatg ctgcagccga   5640
ggccgccaga tccaaccgag tgacagtgtt ccccattgga atcggggatc ggtacagtga   5700 gcccagctg agcagcttgg caggcccaaa ggctggctcc aatatggtaa ggctccagcg    5760
aattgaagac ctccccaccg tggccaccct gggaaattcc ttcttccaca agctgtgctc   5820
tgggtttgat agagtttgcg tggatgagga tgggaatgag aagaggcccg gggatgtctg   5880
gaccttgcca gaccagtgcc acacagtgac ttgcctgcca gatggccaga ccttgctgaa   5940
gagtcatcgg gtcaactgtg accgggggcc aaggccttcg tgccccaatg ccagccccc    6000 tctcagggta gaggagacct gtggctgccg ctggacctgt ccctgtgtgt gcatgggcag   6060
ctctacccgg cacatcgtga cctttgatgg gcagaatttc aagctgactg gcagctgttc   6120
gtatgtccta tttcaaaaca aggagcagga cctggaggtg attctccaga atggtgcctg   6180
cagccctggg gcgaaggaga cctgcatgaa atccattgag gtgaagcatg acggcctctc   6240
agttgagctc cacagtgaca tgcagatgac agtgaatggg agactagtct ccatcccata   6300
tgtgggtgga gacatggaag tcaatgttta tgggaccatc atgtatgagg tcagattcaa   6360
ccatcttggc cacatcttca cattcacccc ccaaaacaat gagttccagc tgcagctcag   6420
ccccaggacc tttgcttcga agacatatgg tctctgtggg atctgtgatg agaacggagc   6480
caatgacttc attctgaggg atgggacagt caccacagac tggaaggcac tcatccagga   6540
atggaccgta cagcagcttg ggaagacatc ccagcctgtc catgaggagc agtgtcctgt   6600
ctccgaattc ttccactgcc aggtcctcct ctcagaattg tttgccgagt gccacaaggt   6660
cctcgctcca gccacctttt atgccatgtg ccagcccgac agttgccacc cgaagaaagt   6720
gtgtgaggcg attgccttgt atgcccacct ctgtcggacc aaagggggtct gtgtggactg   6780 gaggagggcc aatttctgtg ctatgtcatg tccaccatcc ctggtgtaca accactgtga   6840
gcatggctgc cctcggctct gtgaaggcaa tacaagctcc tgtgggacc aaccctcgga    6900 aggctgcttc tgcccccaa accaagtcat gctggaaggt agctgtgtcc cgaggaggc    6960 ctgtacccag tgcatcagcg aggatggagt ccggcaccag ttcctggaaa cctgggtccc   7020
agcccaccag ccttgccaga tctgcacgtg cctcagtggg cggaaggtca actgtacgtt   7080
gcagccctgc cccacagcca agctcccac ctgtggcccg tgtgaagtgg cccgcctccg    7140
ccagaacgca gtgcagtgct gcccggagta cgagtgtgtg tgtgacctgg tgagctgtga   7200
```

-continued

```
cctgccccg gtgcctccct gcgaagatgg cctccagatg accctgacca atcctggcga    7260
gtgcagaccc aacttcacct gtgcctgcag gaaggatgaa tgcagacggg agtccccgcc    7320
ctcttgtccc ccgcaccgga cgccggccct tcggaagact cagtgctgtg atgagtatga    7380
gtgtgcatgc aactgtgtca actccacggt gagctgcccg cttgggtacc tggcctcggc    7440
tgtcaccaac gactgtggct gcaccacaac aacctgcttc cctgacaagg tgtgtgtcca    7500
ccgaggcacc atctaccctg tgggccagtt ctgggaggag gcctgtgacg tgtgcacctg    7560
cacggacttg gaggactctg tgatgggcct gcgtgtggcc cagtgctccc agaagccctg    7620
tgaggacaac tgcctgtcag gcttcactta tgtccttcat gaaggcgagt gctgtggaag    7680
gtgtctgcca tctgcctgtg aggtggtcac tggttcacca cggggcgacg cccagtctca    7740
ctggaagaat gttggctctc actgggcctc ccctgacaac ccctgcctca tcaatgagtg    7800
tgtccgagtg aaggaagagg tctttgtgca acagaggaat gtctcctgcc cccagctgaa    7860
tgtccccacc tgccccacgg gcttccagct gagctgtaag acctcagagt gttgtcccac    7920
ctgtcactgc gagcccctgg aggcctgctt gctcaatggt accatcattg ggccggggaa    7980
aagtctgatg attgatgtgt gtacaacctg ccgctgcacc gtgccggtgg gagtcatctc    8040
tggattcaag ctggagggca ggaagaccac ctgtgaggca tgcccccctgg gttataagga    8100 agagaagaac caaggtgaat gctgtgggag atgtctgcct atagcttgca ccattcagct    8160
aagaggagga cagatcatga cactgaagcg tgatgagact atccaggatg gctgtgacag    8220
tcacttctgc aaggtcaatg aaagaggaga gtacatctgg gagaagagag tcacgggttg    8280
cccacctttc gatgaacaca gtgtctggc tgagggagga aaaatcatga aaattccagg    8340
cacctgctgt gacacatgtg aggagccaga atgcaaggat atcattgcca agctgcagcg    8400
tgtcaaagtg ggagactgta agtctgaaga ggaagtggac attcattact gtgagggtaa    8460
atgtgccagc aaagccgtgt actccatcca catggaggat gtgcaggacc agtgctcctg    8520
ctgctcgccc acccagacgg agcccatgca ggtggccctg cgctgcacca atggctccct    8580
catctaccat gagatcctca atgccatcga atgcaggtgt tcccccagga agtgcagcaa    8640
gtgaggccac tgcctggatg ctactgtcgc ctgccttacc cgacctcact ggactggcca    8700
gagtgctgct cagtcctcct cagtcctcct cctgctctgc tcttgtgctt cctgatccca    8760
caataaaggt caatctttca ccttgaaaaa aaaaaaaaa aa                        8802
```

<210> SEQ ID NO 2
<211> LENGTH: 2813
<212> TYPE: PRT
<213> ORGANISM: Canis familiaris

<400> SEQUENCE: 2

```
Met Ser Pro Thr Arg Leu Val Arg Val Leu Leu Ala Leu Ala Leu Ile
 1               5                  10                  15

Leu Pro Gly Lys Leu Cys Thr Lys Gly Thr Val Gly Arg Ser Ser Met
            20                  25                  30

Ala Arg Cys Ser Leu Leu Gly Gly Asp Phe Ile Asn Thr Phe Asp Glu
        35                  40                  45

Ser Met Tyr Ser Phe Ala Gly Asp Cys Ser Tyr Leu Leu Ala Gly Asp
    50                  55                  60

Cys Gln Glu His Ser Ile Ser Leu Ile Gly Gly Phe Gln Asn Asp Lys
65                  70                  75                  80

Arg Val Ser Leu Ser Val Tyr Leu Gly Glu Phe Phe Asp Ile His Leu
```

-continued

```
                 85                  90                  95
Phe Val Asn Gly Thr Met Leu Gln Gly Thr Gln Ser Ile Ser Met Pro
                100                 105                 110

Tyr Ala Ser Asn Gly Leu Tyr Leu Glu Ala Glu Ala Gly Tyr Tyr Lys
            115                 120                 125

Leu Ser Ser Glu Ala Tyr Gly Phe Val Ala Arg Ile Asp Gly Asn Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Lys Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Arg Cys Lys Arg Val Ser Pro Ser Ser
        195                 200                 205

Pro Cys Asn Val Ser Ser Asp Glu Val Gln Gln Val Leu Trp Glu Gln
        210                 215                 220

Cys Gln Leu Leu Lys Ser Ala Ser Val Phe Ala Arg Cys His Pro Leu
225                 230                 235                 240

Val Asp Pro Glu Pro Phe Val Ala Leu Cys Glu Arg Thr Leu Cys Thr
                245                 250                 255

Cys Val Gln Gly Met Glu Cys Pro Cys Ala Val Leu Leu Glu Tyr Ala
            260                 265                 270

Arg Ala Cys Ala Gln Gln Gly Ile Val Leu Tyr Gly Trp Thr Asp His
        275                 280                 285

Ser Val Cys Arg Pro Ala Cys Pro Ala Gly Met Glu Tyr Lys Glu Cys
        290                 295                 300

Val Ser Pro Cys Thr Arg Thr Cys Gln Ser Leu His Val Lys Glu Val
305                 310                 315                 320

Cys Gln Glu Gln Cys Val Asp Gly Cys Ser Cys Pro Glu Gly Gln Leu
                325                 330                 335

Leu Asp Glu Gly His Cys Val Ser Ala Glu Cys Ser Cys Val His
            340                 345                 350

Ala Gly Gln Arg Tyr Pro Pro Gly Ala Ser Leu Leu Gln Asp Cys His
        355                 360                 365

Thr Cys Ile Cys Arg Asn Ser Leu Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Val Cys His Tyr Leu Leu Ala Gln
            405                 410                 415

Asp Cys Gln Asp His Thr Phe Ser Val Val Ile Glu Thr Val Gln Cys
        420                 425                 430

Ala Asp Asp Leu Asp Ala Val Cys Thr Arg Ser Val Thr Val Arg Leu
        435                 440                 445

Pro Gly His His Asn Ser Leu Val Lys Leu Lys Asn Gly Gly Gly Val
        450                 455                 460

Ser Met Asp Gly Gln Asp Ile Gln Ile Pro Leu Leu Gln Gly Asp Leu
465                 470                 475                 480

Arg Ile Gln His Thr Val Met Ala Ser Val Arg Leu Ser Tyr Gly Glu
            485                 490                 495

Asp Leu Gln Met Asp Ser Asp Val Arg Gly Arg Leu Leu Val Thr Leu
        500                 505                 510
```

-continued

```
Tyr Pro Ala Tyr Ala Gly Lys Thr Cys Gly Arg Gly Asn Tyr Asn
        515                 520                 525
Gly Asn Arg Gly Asp Asp Phe Val Thr Pro Ala Gly Leu Ala Glu Pro
    530                 535                 540
Leu Val Glu Asp Phe Gly Asn Ala Trp Lys Leu Leu Gly Ala Cys Glu
545                 550                 555                 560
Asn Leu Gln Lys Gln His Arg Asp Pro Cys Ser Leu Asn Pro Arg Gln
                565                 570                 575
Ala Arg Phe Ala Glu Glu Ala Cys Ala Leu Leu Thr Ser Ser Lys Phe
            580                 585                 590
Glu Pro Cys His Arg Ala Val Gly Pro Gln Pro Tyr Val Gln Asn Cys
        595                 600                 605
Leu Tyr Asp Val Cys Ser Cys Ser Asp Gly Arg Asp Cys Leu Cys Ser
    610                 615                 620
Ala Val Ala Asn Tyr Ala Ala Ala Val Ala Arg Arg Gly Val His Ile
625                 630                 635                 640
Ala Trp Arg Glu Pro Gly Phe Cys Ala Leu Ser Cys Pro Gln Gly Gln
                645                 650                 655
Val Tyr Leu Gln Cys Gly Thr Pro Cys Asn Met Thr Cys Leu Ser Leu
            660                 665                 670
Ser Tyr Pro Glu Glu Asp Cys Asn Glu Val Cys Leu Glu Ser Cys Phe
        675                 680                 685
Ser Pro Pro Gly Leu Tyr Leu Asp Glu Arg Gly Asp Cys Val Pro Lys
    690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Thr Ser Gly Gly Leu Gly Ser Leu Leu Pro Asn Pro Val
            740                 745                 750
Leu Ser Ser Pro Arg Cys His Arg Ser Lys Arg Ser Leu Ser Cys Arg
        755                 760                 765
Pro Pro Met Val Lys Leu Val Cys Pro Ala Asp Asn Pro Arg Ala Glu
    770                 775                 780
Gly Leu Glu Cys Ala Lys Thr Cys Gln Asn Tyr Asp Leu Gln Cys Met
785                 790                 795                 800
Ser Thr Gly Cys Val Ser Gly Cys Leu Cys Pro Gln Gly Met Val Arg
                805                 810                 815
His Glu Asn Arg Cys Val Ala Leu Glu Arg Cys Pro Cys Phe His Gln
            820                 825                 830
Gly Gln Glu Tyr Ala Pro Gly Glu Thr Val Lys Ile Asp Cys Asn Thr
        835                 840                 845
Cys Val Cys Arg Asp Arg Lys Trp Thr Cys Thr Asp His Val Cys Asp
    850                 855                 860
Ala Thr Cys Ser Ala Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Leu Arg Ile Leu Val Gly Asn Glu
            900                 905                 910
Gly Cys Ser Tyr Pro Ser Val Lys Cys Lys Lys Arg Val Thr Ile Leu
        915                 920                 925
```

-continued

```
Val Glu Gly Gly Glu Ile Glu Leu Phe Asp Gly Glu Val Asn Val Lys
    930                 935                 940

Lys Pro Met Lys Asp Glu Thr His Phe Glu Val Val Glu Ser Gly Gln
945                 950                 955                 960

Tyr Val Ile Leu Leu Gly Lys Ala Leu Ser Val Val Trp Asp His
            965                 970                 975

Arg Leu Ser Ile Ser Val Thr Leu Lys Arg Thr Tyr Gln Glu Gln Val
        980                 985                 990

Cys Gly Leu Cys Gly Asn Phe Asp Gly Ile Gln Asn Asn Asp Phe Thr
            995                 1000                1005

Ser Ser Ser Leu Gln Ile Glu Glu Asp Pro Val Asp Phe Gly Asn Ser
    1010                1015                1020

Trp Lys Val Asn Pro Gln Cys Ala Asp Thr Lys Val Pro Leu Asp
1025                1030                1035                1040

Ser Ser Pro Ala Val Cys His Asn Asn Ile Met Lys Gln Thr Met Val
            1045                1050                1055

Asp Ser Ser Cys Arg Ile Leu Thr Ser Asp Ile Phe Gln Asp Cys Asn
        1060                1065                1070

Arg Leu Val Asp Pro Glu Pro Phe Leu Asp Ile Cys Ile Tyr Asp Thr
        1075                1080                1085

Cys Ser Cys Glu Ser Ile Gly Asp Cys Thr Cys Phe Cys Asp Thr Ile
    1090                1095                1100

Ala Ala Tyr Ala His Val Cys Ala Gln His Gly Lys Val Val Ala Trp
1105                1110                1115                1120

Arg Thr Ala Thr Phe Cys Pro Gln Asn Cys Glu Glu Arg Asn Leu His
            1125                1130                1135

Glu Asn Gly Tyr Glu Cys Glu Trp Arg Tyr Asn Ser Cys Ala Pro Ala
        1140                1145                1150

Cys Pro Ile Thr Cys Gln His Pro Glu Pro Leu Ala Cys Pro Val Gln
        1155                1160                1165

Cys Val Glu Gly Cys His Ala His Cys Pro Pro Gly Lys Ile Leu Asp
    1170                1175                1180

Glu Leu Leu Gln Thr Cys Ile Asp Pro Glu Asp Cys Pro Val Cys Glu
1185                1190                1195                1200

Val Ala Gly Arg Arg Leu Ala Pro Gly Lys Lys Ile Ile Leu Asn Pro
            1205                1210                1215

Ser Asp Pro Glu His Cys Gln Ile Cys Asn Cys Asp Gly Val Asn Phe
        1220                1225                1230

Thr Cys Lys Ala Cys Arg Glu Pro Gly Ser Val Val Pro Pro Thr
        1235                1240                1245

Asp Gly Pro Ile Gly Ser Thr Thr Ser Tyr Val Glu Asp Thr Ser Glu
    1250                1255                1260

Pro Pro Leu His Asp Phe His Cys Ser Arg Leu Leu Asp Leu Val Phe
1265                1270                1275                1280

Leu Leu Asp Gly Ser Ser Lys Leu Ser Glu Asp Glu Phe Glu Val Leu
            1285                1290                1295

Lys Val Phe Val Val Gly Met Met Glu His Leu His Ile Ser Gln Lys
        1300                1305                1310

Arg Ile Arg Val Ala Val Val Glu Tyr His Asp Gly Ser His Ala Tyr
        1315                1320                1325

Ile Glu Leu Lys Asp Arg Lys Arg Pro Ser Glu Leu Arg Arg Ile Thr
    1330                1335                1340

Ser Gln Val Lys Tyr Ala Gly Ser Glu Val Ala Ser Thr Ser Glu Val
```

-continued

```
1345              1350              1355              1360

Leu Lys Tyr Thr Leu Phe Gln Ile Phe Gly Lys Ile Asp Arg Pro Glu
            1365              1370              1375

Ala Ser Arg Ile Ala Leu Leu Leu Met Ala Ser Gln Glu Pro Ser Arg
        1380              1385              1390

Leu Ala Arg Asn Leu Val Arg Tyr Val Gln Gly Leu Lys Lys Lys
        1395              1400              1405

Val Ile Val Ile Pro Val Gly Ile Gly Pro His Ala Ser Leu Lys Gln
    1410              1415              1420

Ile His Leu Ile Glu Lys Gln Ala Pro Glu Asn Lys Ala Phe Val Phe
1425              1430              1435              1440

Ser Gly Val Asp Glu Leu Glu Gln Arg Arg Asp Glu Ile Ile Asn Tyr
            1445              1450              1455

Leu Cys Asp Leu Ala Pro Glu Ala Pro Ala Pro Thr Gln His Pro Pro
        1460              1465              1470

Met Ala Gln Val Thr Val Gly Ser Glu Leu Leu Gly Val Ser Ser Pro
        1475              1480              1485

Gly Pro Lys Arg Asn Ser Met Val Leu Asp Val Val Phe Val Leu Glu
    1490              1495              1500

Gly Ser Asp Lys Ile Gly Glu Ala Asn Phe Asn Lys Ser Arg Glu Phe
1505              1510              1515              1520

Met Glu Glu Val Ile Gln Arg Met Asp Val Gly Gln Asp Arg Ile His
            1525              1530              1535

Val Thr Val Leu Gln Tyr Ser Tyr Met Val Thr Val Glu Tyr Thr Phe
            1540              1545              1550

Ser Glu Ala Gln Ser Lys Gly Glu Val Leu Gln Gln Val Arg Asp Ile
        1555              1560              1565

Arg Tyr Arg Gly Gly Asn Arg Thr Asn Thr Gly Leu Ala Leu Gln Tyr
    1570              1575              1580

Leu Ser Glu His Ser Phe Ser Val Ser Gln Gly Asp Arg Glu Gln Val
1585              1590              1595              1600

Pro Asn Leu Val Tyr Met Val Thr Gly Asn Pro Ala Ser Asp Glu Ile
            1605              1610              1615

Lys Arg Met Pro Gly Asp Ile Gln Val Val Pro Ile Gly Val Gly Pro
        1620              1625              1630

His Ala Asn Val Gln Glu Leu Glu Lys Ile Gly Trp Pro Asn Ala Pro
        1635              1640              1645

Ile Leu Ile His Asp Phe Glu Met Leu Pro Arg Glu Ala Pro Asp Leu
    1650              1655              1660

Val Leu Gln Arg Cys Cys Ser Gly Glu Gly Leu Gln Ile Pro Thr Leu
1665              1670              1675              1680

Ser Pro Thr Pro Asp Cys Ser Gln Pro Leu Asp Val Val Leu Leu Leu
            1685              1690              1695

Asp Gly Ser Ser Ser Ile Pro Ala Ser Tyr Phe Asp Glu Met Lys Ser
            1700              1705              1710

Phe Thr Lys Ala Phe Ile Ser Arg Ala Asn Ile Gly Pro Arg Leu Thr
        1715              1720              1725

Gln Val Ser Val Leu Gln Tyr Gly Ser Ile Thr Thr Ile Asp Val Pro
    1730              1735              1740

Trp Asn Val Ala Tyr Glu Lys Val His Leu Leu Ser Leu Val Asp Leu
1745              1750              1755              1760

Met Gln Gln Glu Gly Gly Pro Ser Glu Ile Gly Asp Ala Leu Ser Phe
            1765              1770              1775
```

-continued

```
Ala Val Arg Tyr Val Thr Ser Glu Val His Gly Ala Arg Pro Gly Ala
        1780                1785                1790

Ser Lys Ala Val Val Ile Leu Val Thr Asp Val Ser Val Asp Ser Val
    1795                1800                1805

Asp Ala Ala Ala Glu Ala Ala Arg Ser Asn Arg Val Thr Val Phe Pro
    1810                1815                1820

Ile Gly Ile Gly Asp Arg Tyr Ser Glu Ala Gln Leu Ser Ser Leu Ala
1825                1830                1835                1840

Gly Pro Lys Ala Gly Ser Asn Met Val Arg Leu Gln Arg Ile Glu Asp
            1845                1850                1855

Leu Pro Thr Val Ala Thr Leu Gly Asn Ser Phe Phe His Lys Leu Cys
        1860                1865                1870

Ser Gly Phe Asp Arg Val Cys Val Asp Glu Asp Gly Asn Glu Lys Arg
        1875                1880                1885

Pro Gly Asp Val Trp Thr Leu Pro Asp Gln Cys His Thr Val Thr Cys
        1890                1895                1900

Leu Pro Asp Gly Gln Thr Leu Leu Lys Ser His Arg Val Asn Cys Asp
1905                1910                1915                1920

Arg Gly Pro Arg Pro Ser Cys Pro Asn Gly Gln Pro Pro Leu Arg Val
            1925                1930                1935

Glu Glu Thr Cys Gly Cys Arg Trp Thr Cys Pro Cys Val Cys Met Gly
            1940                1945                1950

Ser Ser Thr Arg His Ile Val Thr Phe Asp Gly Gln Asn Phe Lys Leu
        1955                1960                1965

Thr Gly Ser Cys Ser Tyr Val Leu Phe Gln Asn Lys Glu Gln Asp Leu
        1970                1975                1980

Glu Val Ile Leu Gln Asn Gly Ala Cys Ser Pro Gly Ala Lys Glu Thr
1985                1990                1995                2000

Cys Met Lys Ser Ile Glu Val Lys His Asp Gly Leu Ser Val Glu Leu
            2005                2010                2015

His Ser Asp Met Gln Met Thr Val Asn Gly Arg Leu Val Ser Ile Pro
            2020                2025                2030

Tyr Val Gly Gly Asp Met Glu Val Asn Val Tyr Gly Thr Ile Met Tyr
        2035                2040                2045

Glu Val Arg Phe Asn His Leu Gly His Ile Phe Thr Phe Thr Pro Gln
    2050                2055                2060

Asn Asn Glu Phe Gln Leu Gln Leu Ser Pro Arg Thr Phe Ala Ser Lys
2065                2070                2075                2080

Thr Tyr Gly Leu Cys Gly Ile Cys Asp Glu Asn Gly Ala Asn Asp Phe
            2085                2090                2095

Ile Leu Arg Asp Gly Thr Val Thr Thr Asp Trp Lys Ala Leu Ile Gln
        2100                2105                2110

Glu Trp Thr Val Gln Gln Leu Gly Lys Thr Ser Gln Pro Val His Glu
        2115                2120                2125

Glu Gln Cys Pro Val Ser Glu Phe Phe His Cys Gln Val Leu Leu Ser
    2130                2135                2140

Glu Leu Phe Ala Glu Cys His Lys Val Leu Ala Pro Ala Thr Phe Tyr
2145                2150                2155                2160

Ala Met Cys Gln Pro Asp Ser Cys His Pro Lys Lys Val Cys Glu Ala
            2165                2170                2175

Ile Ala Leu Tyr Ala His Leu Cys Arg Thr Lys Gly Val Cys Val Asp
        2180                2185                2190
```

-continued

```
Trp Arg Arg Ala Asn Phe Cys Ala Met Ser Cys Pro Pro Ser Leu Val
    2195                2200                2205

Tyr Asn His Cys Glu His Gly Cys Pro Arg Leu Cys Glu Gly Asn Thr
    2210                2215                2220

Ser Ser Cys Gly Asp Gln Pro Ser Glu Gly Cys Phe Cys Pro Pro Asn
2225                2230                2235                2240

Gln Val Met Leu Glu Gly Ser Cys Val Pro Glu Glu Ala Cys Thr Gln
        2245                2250                2255

Cys Ile Ser Glu Asp Gly Val Arg His Gln Phe Leu Glu Thr Trp Val
            2260                2265                2270

Pro Ala His Gln Pro Cys Gln Ile Cys Thr Cys Leu Ser Gly Arg Lys
    2275                2280                2285

Val Asn Cys Thr Leu Gln Pro Cys Pro Thr Ala Lys Ala Pro Thr Cys
    2290                2295                2300

Gly Pro Cys Glu Val Ala Arg Leu Arg Gln Asn Ala Val Gln Cys Cys
2305                2310                2315                2320

Pro Glu Tyr Glu Cys Val Cys Asp Leu Val Ser Cys Asp Leu Pro Pro
            2325                2330                2335

Val Pro Pro Cys Glu Asp Gly Leu Gln Met Thr Leu Thr Asn Pro Gly
        2340                2345                2350

Glu Cys Arg Pro Asn Phe Thr Cys Ala Cys Arg Lys Asp Glu Cys Arg
        2355                2360                2365

Arg Glu Ser Pro Pro Ser Cys Pro Pro His Arg Thr Pro Ala Leu Arg
    2370                2375                2380

Lys Thr Gln Cys Cys Asp Glu Tyr Glu Cys Ala Cys Asn Cys Val Asn
2385                2390                2395                2400

Ser Thr Val Ser Cys Pro Leu Gly Tyr Leu Ala Ser Ala Val Thr Asn
            2405                2410                2415

Asp Cys Gly Cys Thr Thr Thr Thr Cys Phe Pro Asp Lys Val Cys Val
            2420                2425                2430

His Arg Gly Thr Ile Tyr Pro Val Gly Gln Phe Trp Glu Glu Ala Cys
        2435                2440                2445

Asp Val Cys Thr Cys Thr Asp Leu Glu Asp Ser Val Met Gly Leu Arg
    2450                2455                2460

Val Ala Gln Cys Ser Gln Lys Pro Cys Glu Asp Asn Cys Leu Ser Gly
2465                2470                2475                2480

Phe Thr Tyr Val Leu His Glu Gly Glu Cys Cys Gly Arg Cys Leu Pro
        2485                2490                2495

Ser Ala Cys Glu Val Val Thr Gly Ser Pro Arg Gly Asp Ala Gln Ser
            2500                2505                2510

His Trp Lys Asn Val Gly Ser His Trp Ala Ser Pro Asp Asn Pro Cys
        2515                2520                2525

Leu Ile Asn Glu Cys Val Arg Val Lys Glu Glu Val Phe Val Gln Gln
    2530                2535                2540

Arg Asn Val Ser Cys Pro Gln Leu Asn Val Pro Thr Cys Pro Thr Gly
2545                2550                2555                2560

Phe Gln Leu Ser Cys Lys Thr Ser Glu Cys Cys Pro Thr Cys His Cys
            2565                2570                2575

Glu Pro Leu Glu Ala Cys Leu Leu Asn Gly Thr Ile Ile Gly Pro Gly
        2580                2585                2590

Lys Ser Leu Met Ile Asp Val Cys Thr Thr Cys Arg Cys Thr Val Pro
    2595                2600                2605

Val Gly Val Ile Ser Gly Phe Lys Leu Glu Gly Arg Lys Thr Thr Cys
```

-continued

```
           2610                2615                2620
Glu Ala Cys Pro Leu Gly Tyr Lys Glu Glu Lys Asn Gln Gly Glu Cys
2625                2630                2635                2640

Cys Gly Arg Cys Leu Pro Ile Ala Cys Thr Ile Gln Leu Arg Gly Gly
            2645                2650                2655

Gln Ile Met Thr Leu Lys Arg Asp Glu Thr Ile Gln Asp Gly Cys Asp
        2660                2665                2670

Ser His Phe Cys Lys Val Asn Glu Arg Gly Glu Tyr Ile Trp Glu Lys
    2675                2680                2685

Arg Val Thr Gly Cys Pro Pro Phe Asp Glu His Lys Cys Leu Ala Glu
    2690                2695                2700

Gly Gly Lys Ile Met Lys Ile Pro Gly Thr Cys Asp Thr Cys Glu
2705                2710                2715                2720

Glu Pro Glu Cys Lys Asp Ile Ile Ala Lys Leu Gln Arg Val Lys Val
            2725                2730                2735

Gly Asp Cys Lys Ser Glu Glu Val Asp Ile His Tyr Cys Glu Gly
        2740                2745                2750

Lys Cys Ala Ser Lys Ala Val Tyr Ser Ile His Met Glu Asp Val Gln
    2755                2760                2765

Asp Gln Cys Ser Cys Cys Ser Pro Thr Gln Thr Glu Pro Met Gln Val
    2770                2775                2780

Ala Leu Arg Cys Thr Asn Gly Ser Leu Ile Tyr His Glu Ile Leu Asn
2785                2790                2795                2800

Ala Ile Glu Cys Arg Cys Ser Pro Arg Lys Cys Ser Lys
            2805                2810

<210> SEQ ID NO 3
<211> LENGTH: 60
<212> TYPE: DNA
<213> ORGANISM: Canis familiaris

<400> SEQUENCE: 3 aggggtttc caaaatgaca aaagagtgag cctctccgtg tatctcggag aattttttcga    60

<210> SEQ ID NO 4
<211> LENGTH: 60
<212> TYPE: DNA
<213> ORGANISM: Canis familiaris

<400> SEQUENCE: 4
cattcatttg tttgtcaatg gtaccatgct gcaggggacc caaaggtaag tcagaagccc    60

<210> SEQ ID NO 5
<211> LENGTH: 60
<212> TYPE: DNA
<213> ORGANISM: Canis familiaris

<400> SEQUENCE: 5
gaatgttcag gttaatatgg accctgggga tcactttgca accccttgt tttttcagat     60

<210> SEQ ID NO 6
<211> LENGTH: 60
<212> TYPE: DNA
<213> ORGANISM: Canis familiaris

<400> SEQUENCE: 6
gagggagccg ggcccagag acaggaagta aatgtgccca gggaaagtga gtggcaggac    60
```

```
<210> SEQ ID NO 7
<211> LENGTH: 60
<212> TYPE: DNA
<213> ORGANISM: Canis familiaris

<400> SEQUENCE: 7
tgggtgaaag ccccatatcc cgactcctgg tcaaggagac tttgcaccaa ggtcccagcc      60

<210> SEQ ID NO 8
<211> LENGTH: 60
<212> TYPE: DNA
<213> ORGANISM: Canis familiaris

<400> SEQUENCE: 8
ctggagcatg gggttggggt tggaaggtgg agggacatgg aggaaatgca tgagaagcac      60

<210> SEQ ID NO 9
<211> LENGTH: 58
<212> TYPE: DNA
<213> ORGANISM: Canis familiaris

<400> SEQUENCE: 9
gcttcctgag ctcctccttg tcccaccagc atctccatgc cctacgcctc caatgggc        58

<210> SEQ ID NO 10
<211> LENGTH: 24
<212> TYPE: DNA
<213> ORGANISM: Canis familiaris

<400> SEQUENCE: 10
aaatgacaaa agagtgagcc ggtc                                             24

<210> SEQ ID NO 11
<211> LENGTH: 24
<212> TYPE: DNA
<213> ORGANISM: Canis familiaris

<400> SEQUENCE: 11
aagtctcctt gaccagcggt cggg                                             24

<210> SEQ ID NO 12
<211> LENGTH: 35
<212> TYPE: PRT
<213> ORGANISM: Canis familiaris

<400> SEQUENCE: 12

Gly Gly Phe Gln Asn Asp Lys Arg Val Ser Leu Ser Val Tyr Leu Gly
 1               5                  10                  15

Glu Phe Phe Asp Ile His Leu Phe Val Asn Gly Thr Met Leu Gln Gly
                20                  25                  30

Thr Gln Arg
         35

<210> SEQ ID NO 13
<211> LENGTH: 9
<212> TYPE: PRT
<213> ORGANISM: Canis familiaris

<400> SEQUENCE: 13

Ile Ser Met Pro Tyr Ala Ser Asn Gly
 1               5

<210> SEQ ID NO 14
```

-continued

```
<211> LENGTH: 31
<212> TYPE: DNA
<213> ORGANISM: Canis familiaris

<400> SEQUENCE: 14
aggacaactg cctgcctgtc ggtgagtggg g                           31

<210> SEQ ID NO 15
<211> LENGTH: 31
<212> TYPE: DNA
<213> ORGANISM: Canis familiaris

<400> SEQUENCE: 15
aggacaactg cctgcctgtc agtgagtggg g                           31

<210> SEQ ID NO 16
<211> LENGTH: 8
<212> TYPE: DNA
<213> ORGANISM: Canis familiaris

<400> SEQUENCE: 16 aggtragt                                                     8

<210> SEQ ID NO 17
<211> LENGTH: 12
<212> TYPE: DNA
<213> ORGANISM: Canis familiaris

<400> SEQUENCE: 17
ggcttcactt at                                                12

<210> SEQ ID NO 18
<211> LENGTH: 18
<212> TYPE: DNA
<213> ORGANISM: Canis familiaris

<400> SEQUENCE: 18
aggacaactg cctggctt                                          18

<210> SEQ ID NO 19
<211> LENGTH: 15
<212> TYPE: DNA
<213> ORGANISM: Canis familiaris

<400> SEQUENCE: 19
gagcctttgt cgccc                                             15

<210> SEQ ID NO 20
<211> LENGTH: 16
<212> TYPE: DNA
<213> ORGANISM: Canis familiaris

<400> SEQUENCE: 20 gagcctttg tcgccc                                             16

<210> SEQ ID NO 21
<211> LENGTH: 218
<212> TYPE: DNA
<213> ORGANISM: Canis familiaris

<400> SEQUENCE: 21
gtcctgtggg agcagtgcca gctcctgaag agtgcctcgg tgtttgcccg ctgccacccg    60
ctggtggacc ctgagccttt tgtcgccctg tgtgaaagga ctctgtgcac ctgtgtccag   120
```

```
gggatggagt gcccttgtgc ggtcctcctg gagtacgccc gggcctgtgc ccagcaggga      180
attgtgctgt acggctggac cgaccacagc gtctgccg                              218
```

<210> SEQ ID NO 22
<211> LENGTH: 73
<212> TYPE: PRT
<213> ORGANISM: Canis familiaris

<400> SEQUENCE: 22

```
Val Leu Trp Glu Gln Cys Gln Leu Leu Lys Ser Ala Ser Val Phe Ala
 1               5                  10                  15

Arg Cys His Pro Leu Val Asp Pro Glu Pro Phe Val Ala Leu Cys Glu
                20                  25                  30

Arg Thr Leu Cys Thr Cys Val Gln Gly Met Glu Cys Pro Cys Ala Val
            35                  40                  45

Leu Leu Glu Tyr Ala Arg Ala Cys Ala Gln Gln Gly Ile Val Leu Tyr
        50                  55                  60

Gly Trp Thr Asp His Ser Val Cys Arg
 65                  70
```

<210> SEQ ID NO 23
<211> LENGTH: 20
<212> TYPE: DNA
<213> ORGANISM: Canis familiaris

<400> SEQUENCE: 23

```
tcctgtggga gcagtgccag                                                   20
```

<210> SEQ ID NO 24
<211> LENGTH: 11
<212> TYPE: DNA
<213> ORGANISM: Canis familiaris

<400> SEQUENCE: 24

```
gcnnnnnnng c                                                            11
```

<210> SEQ ID NO 25
<211> LENGTH: 18
<212> TYPE: DNA
<213> ORGANISM: Canis familiaris

<400> SEQUENCE: 25

```
gtggtcggtc cagccgta                                                     18
```

<210> SEQ ID NO 26
<211> LENGTH: 20
<212> TYPE: DNA
<213> ORGANISM: Canis familiaris

<400> SEQUENCE: 26

```
tctaccctgt gggccagttc                                                   20
```

<210> SEQ ID NO 27
<211> LENGTH: 19
<212> TYPE: DNA
<213> ORGANISM: Canis familiaris

<400> SEQUENCE: 27

```
gaccacctca caggcagat                                                    19
```

-continued

```
<210> SEQ ID NO 28
<211> LENGTH: 21
<212> TYPE: DNA
<213> ORGANISM: Canis familiaris

<400> SEQUENCE: 28
ctgtgaggac aactgcctgc c                                          21

<210> SEQ ID NO 29
<211> LENGTH: 26
<212> TYPE: DNA
<213> ORGANISM: Canis familiaris

<400> SEQUENCE: 29
tggccctgaa ccggaaatta ctcaag                                     26
```

DNA ENCODING CANINE VON WILLEBRAND FACTOR AND METHODS OF USE

RELATED APPLICATIONS

The present invention is a continuation-in-part of U.S. Ser. No. 08/896,449, filed Jul. 18, 1997, which claims priority from U.S. Ser. No. 60/020,998, filed Jul. 19, 1996, both hereby expressly incorporated by reference.

FIELD OF THE INVENTION

This invention relates generally to canine von Willebrand factor (vWF), and more particularly, to the gene encoding vWF as well as a genetic defect that causes canine von Willebrand's disease.

BACKGROUND OF THE INVENTION

In both dogs and humans, von Willebrand's disease (vWD) is a bleeding disorder of variable severity that results from a quantitative or qualitative defect in von Willebrand factor (vWF) (Ginsburg, D. et al., *Blood* 79:2507–2519 (1992); Ruggeri, Z. M., et al., *FASEB J* 7:308–316 (1993); Dodds, W. J., *Mod Vet Pract* 681–686 (1984); Johnson, G. S. et al., *JAVMA* 176:1261–1263 (1988); Brooks, M., *Probl In Vet Med* 4:636–646 (1992)). This clotting factor has two known functions, stabilization of Factor VIII (hemophilic factor A) in the blood, and aiding the adhesion of platelets to the subendothelium, which allows them to provide hemostasis more effectively. If the factor is missing or defective, the patient, whether human or dog, may bleed severely.

The disease is the most common hereditary bleeding disorder in both species, and is genetically and clinically heterogenous. Three clinical types, called 1, 2, and 3 (formerly I, II, and III; see Sadler, J. E. et al., *Blood* 84:676–679 (1994) for nomenclature changes), have been described. Type 1 vWD is inherited in a dominant, incompletely penetrant fashion. Bleeding appears to be due to the reduced level of vWF rather than a qualitative difference. Although this is the most common form of vWD found in most mammals, and can cause serious bleeding problems, it is generally less severe than the other two types. In addition, a relatively inexpensive vasopressin analog (DDAVP) can help alleviate symptoms (Kraus, K. H. et al., *Vet Surg* 18:103–109 (1989)).

In Type 2 vWD, patients may have essentially normal levels of vWF, but the factor is abnormal as determined by specialized tests (Ruggeri, Z. M., et al., *FASEB J* 7:308–316 (1993); Brooks, M., *Probl In Vet Med* 4:636–646 (1992)). This type is also inherited in a dominant fashion and has only rarely been described in dogs (Turrentine, M. A., et al., *Vet Clin North Am Small Anim Pract* 18:275 (1988)).

Type 3 vWD is the most severe form of the disease. It is inherited as an autosomal recessive trait, and affected individuals have no detectable vWF in their blood. Serious bleeding episodes require transfusions of blood or cryoprecipitate to supply the missing vWF. Heterozygous carriers have moderately reduced factor concentrations, but generally appear to have normal hemostasis.

Scottish terriers have Type 3 vWD (Dodds, W. J., *Mod Vet Pract* 681–686 (1984); Johnson, G. S. et al., *JAVMA* 176:1261–1263 (1988)). Homozygotes have no detectable vWF and have a severe bleeding disorder. Heterozygotes have reduced levels of the factor, and are clinically normal (Brooks, M. et al., *JAVMA* 200:1123–1127 (1992)). The prevalence of vWD among Scottish terriers including both heterozygotes and homozygotes has been variously estimated from 27–31% (Stokol, T. et al., *Res. Vet. Sci.* 59:152–155 (1995); Brooks, M., *Proc. 9th ACVIM Forum* 89–91 (1991)).

Currently, detection of affected and carrier Scottish terrier dogs is done by vWF antigen testing (Benson, R. E. et al., *Am J Vet Res* 44:399–403 (1983); Stokol, T. et al., *Res. Vet. Sci.* 59:152–155 (1995)) or by coagulation assays (Rosborough, T. K. et al., *J. Lab. Clin. Med.* 96:47–56 (1980); Read, M. S. et al., *J. Lab. Clin. Med.* 101:74–82 (1983)). These procedures yield variable results, as the protein-based tests can be influenced by such things as sample collection, sample handling, estrous, pregnancy, vaccination, age, and hypothyroidism (Strauss, H. S. et al., *New Eng J Med* 269:1251–1252 (1963); Bloom, A. L., *Mayo Clin Proc* 66:743–751 (1991); Stirling, Y. et al., *Thromb Haemostasis* 52:176–182 (1984); Mansell, P. D. et al., *Br Vet. J.* 148:329–337 (1992); Avgeris, S. et al., *JAVMA* 196:921–924 (1990); Panciera, D. P. et al., *JAVMA* 205:1550–1553 (1994)). Thus, for example, a dog that tests within the normal range on one day, can test within the carrier range on another day. It is therefore difficult for breeders to use this information.

It would thus be desirable to provide the nucleic acid sequence encoding canine vWF. It would also be desirable to provide the genetic defect responsible for canine vWD. It would further be desirable to obtain the amino acid sequence of canine vWF. It would also be desirable to provide a method for detecting carriers of the defective vWF gene based on the nucleic acid sequence of the normal and defective vWF gene.

SUMMARY OF THE INVENTION

The present invention provides a novel purified and isolated nucleic acid sequence encoding canine vWF. Nucleic acid sequences containing the mutations that cause vWD in Scottish terriers, Doberman pinschers, Shetland sheepdogs, Manchester terriers and Poodles are also provided. The nucleic acid sequences of the present invention may be used in methods for detecting carriers of the mutation that causes vWD. Such methods may be used by breeders to reduce the frequency of the disease-causing allele and the incidence of disease. In addition, the nucleic acid sequence of the canine vWF provided herein may be used to determine the genetic defect that causes vWD in other breeds as well as other species.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which:

FIGS. 1A–1C is the nucleic acid sequence of the canine von Willebrand factor of the present invention (SEQ ID NO: 1);

FIGS. 2A–2C is a comparison of the human and canine prepro-von Willebrand factor amino acid sequences (SEQ ID NO: 2);

FIG. 4 illustrates the results of a method of the present invention used to detect the Scottish terrier vWD mutation (SEQ ID NOS: 3–13);

FIG. 6 is an illustration showing the splice site comparison between normal and mutant Doberman pinscher vWF alleles (SEQ ID NOS: 14–17);

FIG. 11 is a diagram illustrating the Mwo I diagnostic test for the Shetland sheepdog Type 3 vWD mutation (SEQ ID NOS: 21–25)

DETAILED DESCRIPTION OF THE PREFERRED EMBODIMENTS

Figure 3:
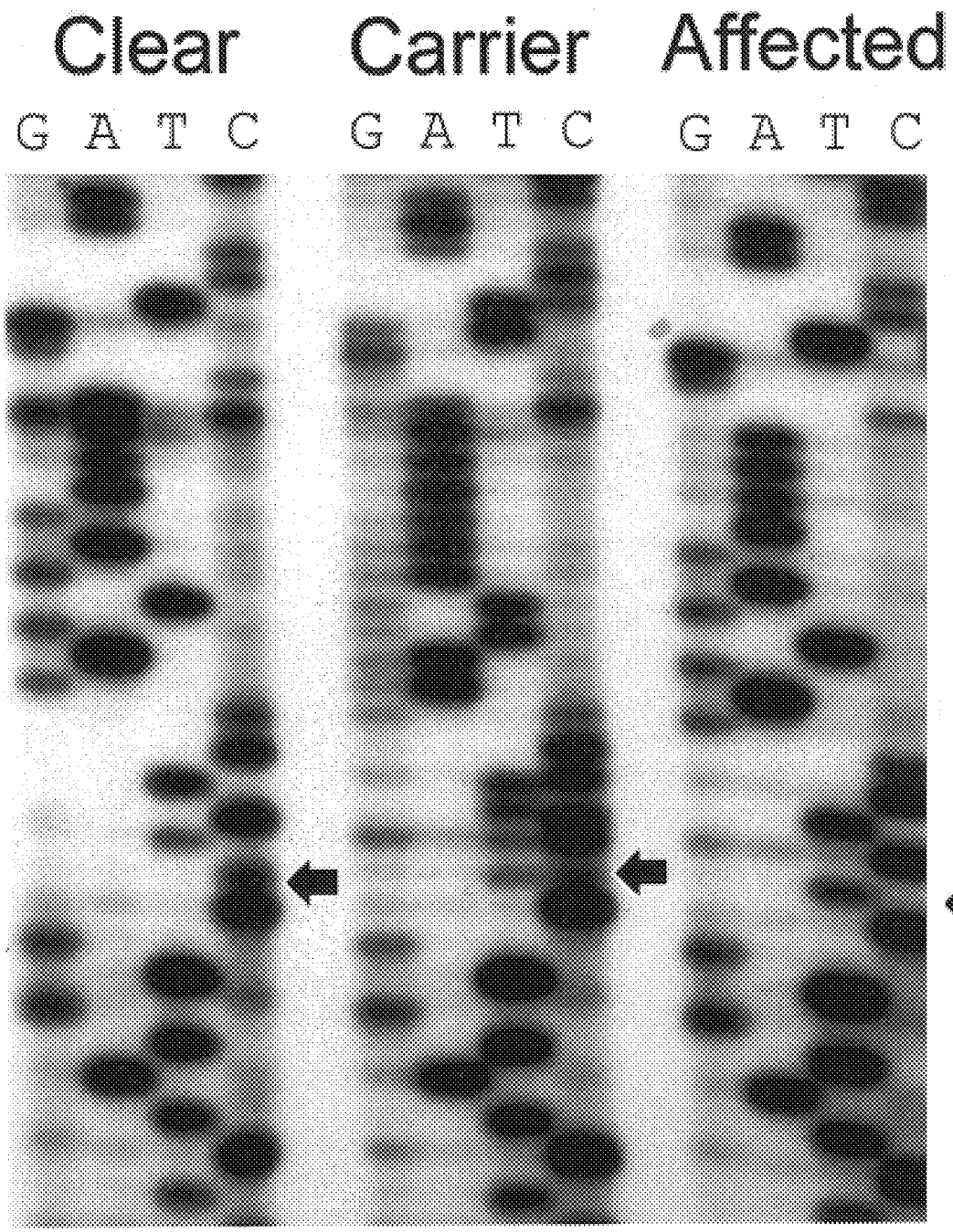
FIG. 3 provides nucleotide sequencing ladders for the von Willebrand's disease mutation region for normal (clear), carrier, and affected Scottish terriers, the sequences being obtained directly from PCR products derived from genomic DNAs in exon 4.

The cDNA encoding canine von Willebrand Factor (vWF) has been sequenced, and is set forth in FIGS. 1A–1C and SEQ ID NO: 1. The deduced amino acid sequence is set forth in FIGS. 2A–2C and SEQ ID NO: 2. In one embodiment, the mutation of the normal vWF gene which causes von Willebrand's Disease (vWD) in Scottish terriers, a deletion at codon 88 of the normal gene resulting in a frameshift, is provided. In another embodiment, a splice junction mutation at nucleotide position 7639 of the normal gene, which causes vWD in Doberman pinschers, Manchester terriers and Poodles, is provided. In yet another embodiment, a single base deletion at nucleotide position 937 of the normal gene, causing vWD in Shetland sheepdogs, is provided. The nucleic acid sequences of the present invention may be used in methods for detecting homozygous and heterozygous carriers of the defective vWF gene.

In a preferred method of detecting the presence of the von Willebrand allele in canines, DNA samples are first collected by relatively noninvasive techniques, i.e., DNA samples are obtained with minimal penetration into body tissues of the animals to be tested. Common noninvasive tissue sample collection methods may be used and include withdrawing buccal cells via cheek swabs and withdrawing blood samples. Following isolation of the DNA by standard techniques, PCR is performed on the DNA utilizing pre-designed primers that produce enzyme restriction sites on those DNA samples that harbor the defective gene. Treatment of the amplified DNA with appropriate restriction enzymes such as BsiE I thus allows one to analyze for the presence of the defective allele. One skilled in the art will appreciate that this method may be applied not only to Scottish terriers, Doberman pinschers, Shetland sheepdogs, Manchester terriers and Poodles, but to other breeds such as Dutch Kooikers, as well.

The presence of the von Willebrand allele in canines can also be detected utilizing ligation amplification reaction technology (LAR) known to those skilled in the art. LAR is a method analogous to PCR for DNA amplification wherein ligases are employed for elongation in place of polymerases used for PCR. Another alternate method for detecting the presence of the canine von Willebrand allele also known to those skilled in the art, is allele specific oligonucleotide hybridization, wherein an oligonucleotide of about 20 bp containing the contiguous nucleotides of the allele of interest is hybridized to the canine DNA.

The present invention provides breeders with an accurate, definitive test whereby the undesired, defective vWF gene may be eliminated from breeding lines. The current tests used by breeders are protein-based, and as noted previously, the primary difficulty with this type of test is the variability of results due to a variety of factors. The ultimate result of such variability is that an inordinate number of animals fall into an ambiguous grouping whereby carriers and noncarriers cannot be reliably distinguished. The present invention obviates the inherent limitations of protein-based tests by detecting the genetic mutation which causes vWD. As described in the Specific Examples, the methods of the present invention provide an accurate test for distinguishing noncarriers, homozygous carriers and heterozygous carriers of the defective vWF gene.

It will be appreciated that because the vWF cDNA of the present invention is substantially homologous to vWF cDNA throughout the canine species, the nucleic acid sequences of the present invention may be used to detect DNA mutations in other breeds as well. In addition, the canine vWF sequence presented herein potentially in combination with the established human sequence (Genbank Accession No. X04385, Bonthron, D. et al., *Nucleic Acids Res.* 14:7125–7128 (1986); Mancuso, D. J. et al., *Biochemistry* 30:253–269 (1989); Meyer, D. et al., *Throm Haemostasis* 70:99–104 (1993)), may be used to facilitate sequencing of the vWF gene and genetic defects causing vWD, in other mammalian species e.g., by using cross-species PCR methods known by those skilled in the art.

It is also within the contemplation of this invention that the isolated and purified nucleic acid sequences of the present invention be incorporated into an appropriate recombinant expression vector, e.g., viral or plasmid, which is capable of transforming an appropriate host cell, either eukaryotic (e.g., mammalian) or prokaryotic (e.g., *E. coli*). Such DNA may involve alternate nucleic acid forms, such as cDNA, gDNA, and DNA prepared by partial or total chemical synthesis. The DNA may also be accompanied by additional regulatory elements, such as promoters, operators and regulators, which are necessary and/or may enhance the expression of the vWF gene product. In this way, cells may be induced to over-express the vWF gene, thereby generating desired amounts of the target vWF protein. It is further contemplated that the canine vWF polypeptide sequence of the present invention may be utilized to manufacture canine vWF using standard synthetic methods.

One skilled in the art will appreciate that the defective protein encoded by the defective vWF gene of the present invention may also be of use in formulating a complementary diagnostic test for canine vWD that may provide further data in establishing the presence of the defective allele. Thus, production of the defective vWF polypeptide, either through expression in transformed host cells as described above for the active vWF polypeptide or through chemical synthesis, is also contemplated by the present invention.

The term "gene" as to referred herein means a nucleic acid which encodes a protein product. The term "nucleic acid"

refers to a linear array of nucleotides and nucleosides, such as genomic DNA, cDNA and DNA prepared by partial or total chemical synthesis from nucleotides. The term "encoding" means that the nucleic acid may be transcribed and translated into the desired polypeptide. "Polypeptide" refers to amino acid sequences which comprise both full-length proteins and fragments thereof. "Mutation" as referred to herein includes any alteration in a nucleic acid sequence including, but not limited to, deletions, substitutions and additions.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID NO: 1 or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in *Current Protocols in Molecular Biology*, John Wiley & Sons, NY (1989), 6.31–6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 65° C. Other stringency parameters are described in Maniatis, T., et al., *Molecular Cloning: A Laboratory Manual*, Cold Spring Harbor Laboratory Press, Cold Spring N.Y., (1982), at pp. 387–389; see also Sambrook J. et al., *Molecular Cloning: A Laboratory Manual*, Second Edition, Volume 2, Cold Spring Harbor Laboratory Press, Cold Spring, N.Y. at pp. 8.46–8.47 (1989).

SPECIFIC EXAMPLE 1

Scottish Terriers

Materials And Methods

Isolation of RNA. The source of the RNA was a uterus from a Scottish Terrier affected with vWD (factor level<0.1% and a clinical bleeder), that was surgically removed because of infection. Spleen tissue was obtained from a Doberman pinscher affected with vWD that died from dilated cardiomyopathy (factor level 7% and a clinical bleeder). Total RNA was extracted from the tissues using Trizol (Life Technologies, Gaithersburg, Md.). The integrity of the RNA was assessed by agarose gel electrophoresis.

Design of PCR primer sets. Primers were designed to a few regions of the gene, where sequences from two species were available (Lavergne, J. M. et al., *Biochem Biophys Res Commun* 194:1019–1024 (1993); Bakhshi, M. R. et al., *Biochem Biophys Acta* 1132:325–328 (1992)). These primers were designed using rules for cross-species' amplifications (Venta et al., "Gene-Specific Universal Mammalian Sequence-Tagged Sites: Application To The Canine Genome" *Biochem. Genet.* 34:321–341 (1996)). Most of the primers had to be designed to other regions of the gene using the human sequence alone (Mancuso, D. J. et al., *Biochemistry* 30:253–269 (1991)). Good amplification conditions canine genomic DNAs.

Reverse Transcriptase-PCR. Total RNA was reverse transcribed using random primers (Bergenhem, N. C. H. et al., *PNAS (USA)* 89:8789–8802 (1992)). The cDNA was amplified using the primer sets shown to work on canine genomic DNA.

DNA Sequence Analysis. Amplification products of the predicted sizes were isolated from agarose gels by adsorption onto silica gel particles using the manufacturer's method (Qiagen, Chatsworth, Calif.). Sequences were determined using $^{33}$P-5' end-labeled primers and a cycle sequencing kit (United States Biochemical Corp., Cleveland, Ohio). The sequences of the 5' and 3' untranslated regions were determined after amplification using Marathon™ RACE kits (Clontech, Palo Alto, Calif.). Sequences were aligned using the Eugene software analysis package (Lark Technologies, Houston, Tex.). The sequence of the canine intron four was determined from PCR-amplified genomic DNA.

Design of a Diagnostic Test. PCR mutagenesis was used to create diagnostic and control BsiE I and Sau96 I restriction enzyme sites for the test. Amplification conditions for the test are: 94° C., 1 min, 61° C., 1 min, and 72° C., 1 min, for 50 cycles using cheek swab DNA (Richards, B. et al., *Human Molecular Genetics* 2:159–163 (1992)).

Population Survey. DNA was collected from 87 Scottish terriers from 16 pedigrees. DNA was isolated either from blood using standard procedures (Sambrook, J. et al., Cold Harbor Spring Lab, Cold Harbor Spring N.Y., 2nd Edition, (1989)) or by cheek swab samples (Richards, B. et al., *Human Molecular Genetics* 2:159–163 (1992)). The genetic status of each animal in the survey was determined using the BsiE I test described above.

Results

Comparison of the canine and human sequences. The alignment of the canine and human prepro-von Willebrand Factor amino acid sequences is shown in FIGS. 2A–2C (SEQ ID NO: 2). The location of the Scottish terrier vWD mutation is indicated by the "*". Potential N-glycosylation sites are shown in bold type. The known and postulated integrin binding sites are boxed. Amino acid numbers are shown on the right side of the figure. The human sequence is derived from Genbank accession number X04385.

Overall, 85.1% sequence identity is seen between the prepro-vWF sequences. The pro-region is slightly less conserved than the mature protein (81.4% vs. 87.5%). There were no other noteworthy percentage sequence identity differences seen in other regions of the gene, or between the known repeats contained within the gene (data not shown). Fourteen potential N-linked glycosylation sites are present in the canine sequence, all of which correspond to similar sites contained within the human sequence. The two integrin binding sites identified in the human vWF protein sequence (Lankhof, H. et al., *Blood* 86:1035–1042 (1995)) are conserved in the canine sequence as well (FIGS. 2A–2C; SEQ ID NO: 2). The 5' and 3' untranslated regions have diverged to a greater extent than the coding region (data not shown), comparable to that found between the human and bovine sequences derived for the 5' flanking region (Janel, N. et al., *Gene* 167:291–295 (1995)). Additional insights into the structure and function of the von Willebrand factor can be gained by comparison of the complete human sequence (Genbank Accession No. XO4385; Bonthron, D. et al., *Nucleic Acids Res.* 14:7125–7128 (1986); Mancuso, D.J. et al., *Biochemistry* 30:253–269 (1989); Meyer, D. et al., *Throm Haemostasis* 70:99–104 (1993)) and the complete canine sequence reported here.

The sequence for most of exon 28 was determined (Mancuso, D. J. et al., *Thromb Haemost* 69:980 (1993); Porter, C. A. et al., *Mol Phylogenet Evol* 5:89–101 (1996)). All three sequences are in complete agreement, although two silent variants have been found in other breeds (Table 1, exon 28). Partial sequences of exons 40 and 41 (cDNA nucleotide numbers 6923 to 7155, from the initiation codon) were also determined as part of the development of a polymorphic simple tandem repeat genetic marker (Shibuya, H. et al., *Anim Genet* 24:122 (1994)). There is a single nucleotide sequence difference between this sequence ("T") and the sequence of the present invention, ("C") at nucleotide position 6928.

Scottish Terrier vWD mutation. FIG. 3 shows nucleotide sequencing ladders for the vWD mutation region for normal (clear), carrier, and affected Scottish terriers. The sequences were obtained directly from PCR products derived from genomic DNAs in exon 4. The arrowheads show the location of the C nucleotide that is deleted in the disease-causing allele. Note that in the carrier ladder each base above the point of the mutation has a doublet appearance, as predicted for deletion mutations. The factor levels reported for these animals were: Normal, 54%; Carrier, 34%; Affected, <0.1%.

As a result of the deletion, a frameshift mutation at codon 88 leads to a new stop codon 103 bases downstream. The resulting severely truncated protein of 119 amino acids does not include any of the mature vWF region. The identity of the base in the normal allele was determined from an unaffected dog.

Development of a diagnostic test. A PCR primer was designed to produce a BsiE I site in the mutant allele but not in the normal allele (FIG. 4; SEQ ID NOS 3 and 10). The position of the deleted nucleotide is indicated by an asterisk. The altered nucleotides in each primer are underlined. The normal and mutant allele can also be distinguished using Sau96 I. The naturally occurring Sau96 I sites are shown by double underlines. The highly conserved donor and acceptor dinucleotide splice sequences are shown in bold type.

In order to ensure that the restriction enzyme cut the amplified DNA to completion, an internal control restriction site common to both alleles was designed into the non-diagnostic primer. The test was verified by digestion of the DNA from animals that were affected, obligate carriers, or normal (based on high factor levels [greater than 100% of normal] obtained from commonly used testing labs and reported by the owners, and also using breeds in which Type 3 vWD has not been observed). The expected results were obtained (e.g., FIG. 5). Five vWD-affected animals from a colony founded from Scottish terriers (Brinkhous, K. M. et al., *Ann. New York Acad. Sci.* 370:191–203 (1981)) were also shown to be homozygous for this mutation. An additional unaffected animal from this same colony was found to be clear.

It would still be possible to misinterpret the results of the test if restriction enzyme digestion was not complete, and if the rates of cleavage of the control and diagnostic sites were vastly different. The rates of cleavage of the two BsiE I sites were thus examined by partially digesting the PCR products and running them on capillary electrophoresis. The rates were found to be very nearly equal (the diagnostic site is cut 12% faster than the control site).

The mutagenesis primer was also designed to produce a Sau96 I site into the normal allele but not the mutant allele. This is the reverse relationship compared to the BsiE I-dependent test, with respect to which allele is cut. Natural internal Sau96 I sites serve as digestion control sites (shown in FIG. 4). The test using this enzyme produced identical genotypic results compared to the BsiE I for all animals examined (data not shown).

Figure 5:
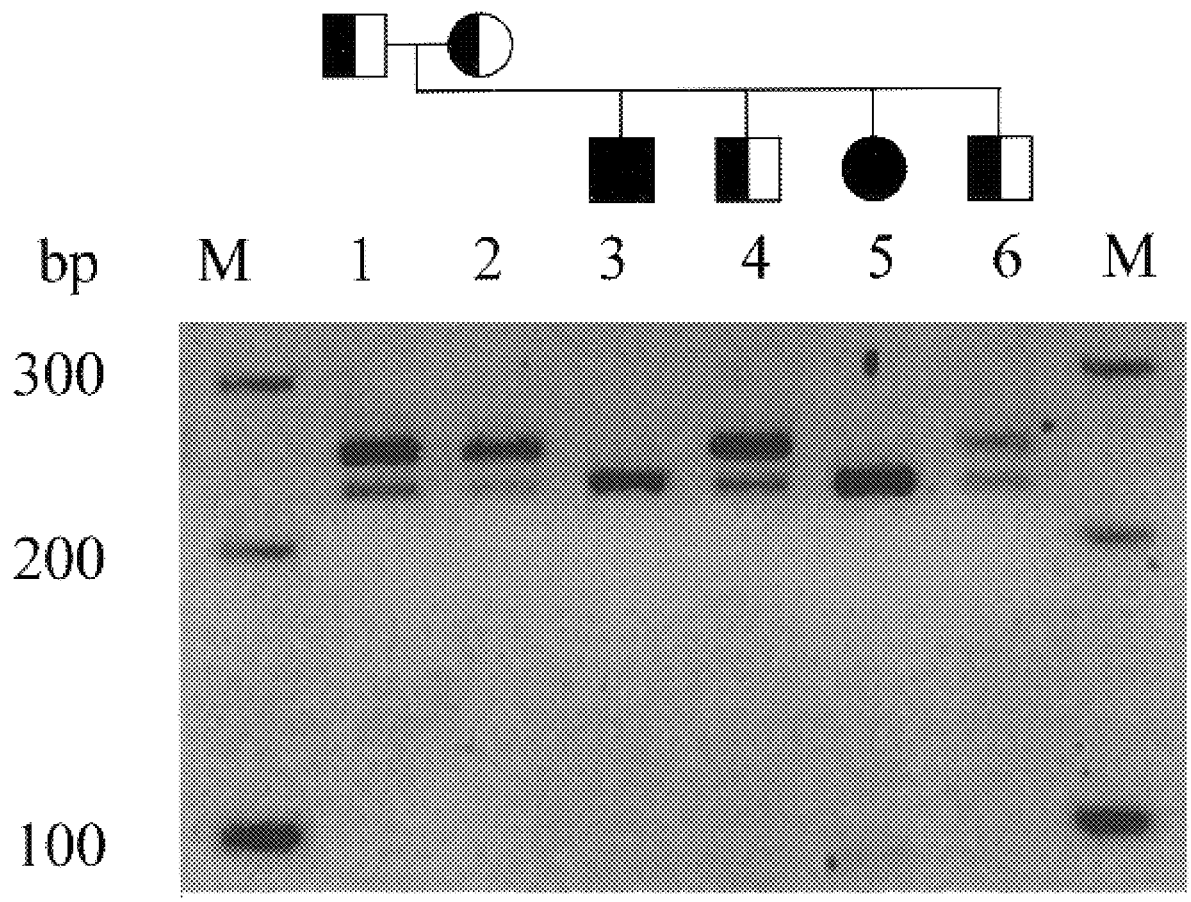
FIG. 5 shows the Scottish terrier pedigree, which in turn illustrates segregation of the mutant and normal vWF alleles.

Mendelian inheritance. One test often used to verify the correct identification of a mutant allele is its inheritance according to Mendel's law of segregation. Three pedigrees were examined in which the normal and mutant alleles were segregating, as shown in FIG. 5. Exon four of the vWF gene was PCR-amplified from genomic DNA. The PCR products were examined for the presence of the normal and mutant vWF alleles by agarose gel electrophoresis after digestion with BsiE I (see FIG. 5). The affected animals are homozygous for the mutant allele (229 bp; lanes 3 and 5). The other animals in this pedigree are heterozygotes (251 bp and 229 bp; lanes 1, 2, 4, and 6), including the obligate carrier parents.

TABLE 1

Differences Between Scottie And Doberman Pinscher Protein And Nucleotide von Willebrand Factor Sequences With Comparison To The Human Sequences

| | | Amino Acid | | | Codon | | |
|---|---|---|---|---|---|---|---|
| Exon | A.A.[1] | Human | Scottie | Doberman | Human | Scottie | Doberman |
| 5' UT[2] | nuc - 35[3] | N/A[4] | N/A | N/A | N/A | A | G |
| 4 | 85 | S | S/F.Shift[5] | S | TCC | TCC/TC— | TCC |
| 5 | 173 | M | R | K | ATG | AGG | AAG |

TABLE 1-continued

Differences Between Scottie And Doberman Pinscher
Protein And Nucleotide von Willebrand Factor Sequences
With Comparison To The Human Sequences

| | | Amino Acid | | | Codon | | |
|---|---|---|---|---|---|---|---|
| Exon | A.A.[1] | Human | Scottie | Doberman | Human | Scottie | Doberman |
| 11 | 422 | S | T | T | TCC | ACA | ACC |
| 21 | 898 | C | C | C | TGC | TGT | TGC |
| 21 | 905 | F | F | L | TTT | TTC | TTA |
| 24 | 1041 | S | S | S | TCA | TCA | TCG |
| 24 | 1042 | S | S | S | TCC | TCC | TCA |
| 28 | 1333 | D | D | E | GAC | GAC | GAG |
| 28 | 1349 | Y | Y | Y | TAT | TAT | TAC* |
| 42 | 2381 | P | L | P | CCC | CTG | CCG |
| 43 | 2479[6] | S | S | S | TCG | TCG | TCA |
| 45 | 2555 | P | P | P | CCC | CCC | CCG |
| 47 | 2591 | P | P | P | CCC | CCT | CCC |
| 49 | 2672 | D | D | D | GAT | GAT | GAC |
| 51 | 2744 | E | E | E | GAG | GAG | GAA |

[1]Amino acid residue position
[2]Untranslated region
[3]Nucleotide position
[4]Not Applicable
[5]Frameshift mutation
[6]Splice site mutation for Doberman pinscher, Manchester terrier and Poodle
Boxed residues show amino acid differences between breeds
*This site has been shown to be polymorphic in some breeds
The mature VWF protein begins in exon 18

The alleles, as typed by both the BsiE I and Sau96 I tests, showed no inconsistencies with Mendelian inheritance. One of these pedigrees included two affected animals, two phenotypically normal siblings, and the obligate carrier parents. The two parents were found to be heterozygous by the test, the two affected animals were found to be homozygous for the mutant allele, and the normal siblings were found to be heterozygotes.

Population survey for the mutation. Cheek swabs or blood samples were collected from 87 animals in order to determine the incidence of carriers in the U.S. Scottish terrier population. Although an attempt was made to make the sample as random as possible, these dogs were found to come from 16 pedigrees, several of which are more distantly interconnected. This is due to some ascertainment bias, based on ownership (as opposed to phenotypic ascertainment bias). In these 87 animals, 4 affected and 15 carrier animals were found.

Discussion

These results establish that the single base deletion found in exon four of the vWF gene causes vWD in the Scottish terrier breed. The protein produced from the mutant allele is extremely short and does not include any of the mature vWF protein. Four Scottish terriers known to be affected with the disease are homozygous for the mutation. Five other mixed-breed dogs descended from Scottish terriers, and affected with vWD, are also homozygous for the mutation. No normal animals are homozygous for the mutation. Unaffected obligate carriers are always heterozygous for the mutation.

The gene frequency, as determined from the population survey, appears to be around 0.13 resulting in a heterozygote frequency of about 23% and expected frequency of affected animals of about 2%. Although the sample size is relatively small and somewhat biased, these data are in general agreement with the protein-based surveys (Stokol, T. et al., *Res Vet Sci* 59:152–155 (1995); Brooks, M., *Probl In Vet Med* 4:636–646 (1992)), in that the allele frequency is substantial.

All data collected thus far indicate that this mutation may account for essentially all of the von Willebrand's disease found in Scottish terriers. This result is consistent with the results found for other genetic diseases, defined at the molecular level, in various domestic animals (Shuster, D. E. et al., *PNAS (USA)* 89:9225–9229 (1992); Rudolph, J. A. et al., *Nat Genet* 2:144–147 (1992); O'Brien, P. J. et al., *JAVMA* 203:842–851 (1993)). A likely explanation may be found in the pronounced founder effect that occurs in domestic animals, compared to most human and wild animal populations.

Published data using the protein-based factor assays have shown that, at least in several instances, obligate carriers have had factor levels that would lead to a diagnosis of "clear" of the disease allele. For example, in one study an obligate carrier had a factor level of 78% (Johnson, G. S. et al., *JAVMA* 176:1261–1263 (1980)). In another study, at least some of the obligate carriers had factor levels of 65% or greater (Brinkhous, K. M. et al., *Ann. New York Acad. Sci.* 370:191–203 (1981)). In addition, the number of animals that fall into an equivocal range can be substantial. In one study, 19% of Scottish terriers fell in this range (50–65% of the normal vWF antigen level) (Stokol, T. et al., *Res Vet Sci* 59:152–155 (1995)). Thus, although the protein-based tests have been useful, the certainty of the DNA-based test described herein should relieve the necessity of repeated testing and the variability associated with the protein-based assays.

The mutation is present in the pre-vWF part of the molecule. This part of the molecule is processed off prior to delivery of the mature protein into the plasma. This pre-portion of the molecule is important for the assembly of the mature vWF protein (Verwiej, L. et al., *EBMO J* 6:2885–2890 (1987); Wise, R.J. et al., *Cell* 52:229–236 (1988)). With the Scottish terrier frameshift vWD mutation, neither this pre-portion nor any of the mature factor is ever produced, in keeping with the fact that no factor has ever been detected in the blood of affected dogs.

The determination of the complete canine vWF cDNA sequence will have an impact upon the development of carrier tests for other breeds and other species as well. Currently, Shetland sheepdogs (see Specific Example 3) and Dutch Kooikers are known to have a significant amount of Type 3 vWD (Brooks, M. et al., *JAVMA* 200:1123–1127 (1992); Slappendel, R. J., *Vet-Q* 17:S21–S22 (1995)). Type 3 vWD has occasionally be seen in other breeds as well (e.g., Johnson, G. S. et al., *JAVMA* 176:1261–1263 (1980)). All Type 3 vWD mutations described in humans to date have been found within the vWF gene itself. The availability of the canine sequence will make it easier to find the mutations in these breeds. In addition, at least some Type 1 mutations have been found within the human vWF gene, and thus Type 1 mutations may also be found within the vWF gene for breeds affected with that form of the disease. The availability of two divergent mammalian vWF cDNA sequences will also make it much easier to sequence the gene from other mammalian species using cross-species PCR methods (e.g., Venta et al., *Biochem. Genet.* 34:321–341 (1996)).

The test described herein for the detection of the mutation in Scottish terriers may be performed on small amounts of DNA from any tissue. The tissues that are the least invasive to obtain are blood and buccal cells. For maximum convenience, a cheek swab as a source of DNA is preferred.

SPECIFIC EXAMPLE 2
Doberman Pinscher

Materials and Methods

RT-PCR and DNA Sequence Analysis. RNA was isolated by using Trizol (Life Technologies, Gaitherburg, Md.) from the spleen of a Doberman pinscher that was affected with vWD (factor value of 7% of normal) and that had died from dilated cardiomyopathy. RT-PCR was performed as previously described using primers to the canine vWF cDNA. Most PCR products were determined directly using a cycle sequencing kit (Amersham Corp, Chicago, Ill.). A minor band containing the four base deletion (see Results) was subcloned into a plasmid vector prior to sequence analysis. The five kb intron 43 was amplified using a commercially available kit for long PCR (Boehringer-Mannheim, Indianapolis, Ind.). The cycling times and temperatures were as follows: initial denaturation, 93° C., 2 min; 10 cycles of 93° C., 15 sec, 62° C., 30 sec, 68° C., 4 min; 20 cycles of 93° C., 15 sec, 62° C., 30 sec, 68° C., 4 min with 20 additional sec per cycle. This was followed by a final extension at 68° C. for 7 min. The sequences of the primers used were: exon 43 (sense primer), 5'-TCTACCCTGTGGGCCAGTTC-3' (SEQ ID NO: 26), and exon 44 (antisense primer), 5'-GACCACCTCACAGGCAGAT-3' (SEQ ID NO: 27).

PCR-Based Mutation Test. PCR mutagenesis was used to create an Msp I site in the normal allele but not in the mutant allele. An internal Msp I digestion control site was also created by PCR mutagenesis within the anti-sense primer, whose target is within intron 43. The control site is contained within the amplification products of both alleles. The sequences of the primers are: diagnostic (sense) primer, 5'-CTGTGAGGACAACTGCCTGCC-3' (SEQ ID NO: 28); and common (anti-sense) primer, 5'-TGGCCCTGAAC CGGAAATTACTCAAG-3' (SEQ ID NO: 29) (the altered bases within each primer are underlined). A 'touchdown' PCR protocol was used for the amplification. The amplification conditions are: 94° C., 30 sec, 63 to 55° C., 40 sec, and 72° C., 50 sec, for the first 8 cycles, with the annealing temperature dropping one degree per cycle. Twenty-eight additional cycles were run, with the annealing temperature held at 55° C. The DNA was digested with Msp I after PCR amplification.

Population Survey. Owners who participated in a population survey supplied cheek swabs from their dogs for genotype analysis. Richards, B. et al., *Hum. Mol Genet.* 2:159 (1992). A number of these dogs had associated vWF values that were determined by various testing laboratories that provide this service to breeders.

Results

During the sequence analysis of the vWF mRNA from an affected Doberman pinscher, a significant nucleotide difference from the Scottish terrier sequence was discovered. This change was found at the last base of exon 43 (nucleotide 7437 from the initiation codon, at amino acid position Ser 2479; G in Scotties, A in the affected Doberman) (Table 1). Although this is a silent amino acid change, it causes the splice junction to be less similar to the mammalian splice junction consensus. Nakai, K. et al., *Gene* 141:171 (1994); Krawcsak, M. et al., *Genet.* 90:41 (1992). Just upstream of the normal splice junction is another sequence that also has significant similarity to the consensus, which is increased by the A at nucleotide position 7437 (FIG. 6; SEQ ID NOS: 14–17). The A at the end of exon 43 could cause the normal splice junction to be used less frequently, and that the upstream cryptic splice site becomes the one predominantly used. Comparison of the splice sites by a devised statistical method (Shapiro, M. B. et al., Nucleic Acids Res. 15:7155 (1987)) gave the following scores: normal splice position with the wild-type allele (G at 7536), 83.9; cryptic splice site with the wild-type allele, 60.6; normal splice position with the mutant allele (A at 7437), 72.2; cryptic splice site with the mutant allele, 70.5. Higher scores represent a greater likelihood of splicing potential. The scores for the normal and cryptic splice sites are quite different with the wild-type allele, but are very close with the mutant allele. These results support the probability of a decreased likelihood for splicing at the normal site, and an increased potential for splicing at the cryptic site with the mutant allele.

A faint RT-PCR band just below the major band from which the variant nucleotide had been detected was observed. This minor band was missing the four bases at the end of exon 43 as confirmed by sequence analysis (FIG. 7;

SEQ ID NO: 18). The position of the four deleted bases is shown on the right side of FIG. 7 (SEQ ID NO: 18).

Figure 8:
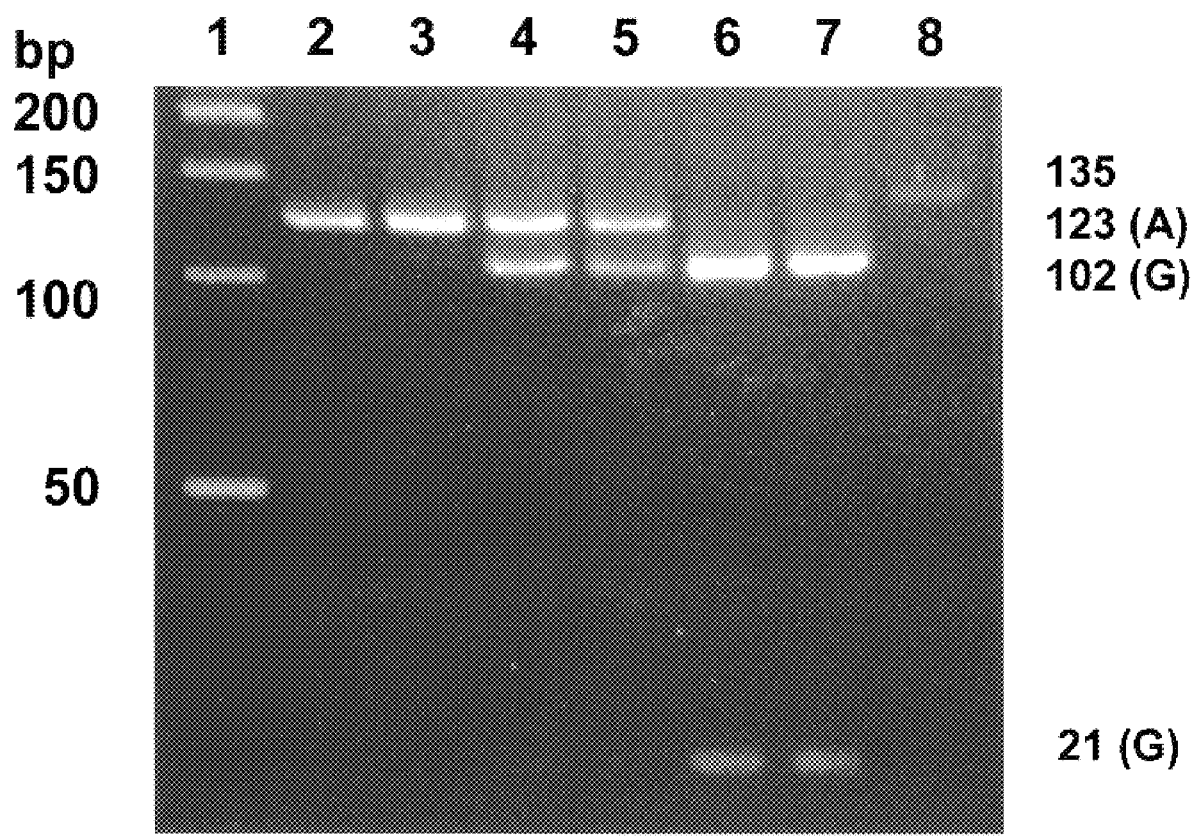
FIG. 8 is a photograph of an agarose gel showing representative results of the PCR-based diagnostic test.

A PCR-based test was developed to detect the nucleotide difference in genomic DNA as described herein in Materials and Methods. The results of the test for several animals with a spectrum of factor values yield a significant correlation between genotype and factor value as shown in FIG. 8. Lane 1 contains a 50 bp ladder as a size marker. The uncut PCR product is 135 bp (lane 8). Both alleles contain a common Msp I restriction site that serves as an internal digestion control. The mutant (A) and normal (G) alleles are represented by the 123 bp and 102 bp bands, respectively. Reported factor levels and deduced genotypic status for dogs represented in the additional lanes are as follows: 2, 12%, affected (AA); 3, 8%, affected (AA); 4, 39%, carrier (AG); 5, 68%, carrier (AG); 6, 125%, homozygous normal (GG); 7, 136%, homozygous normal (GG). A survey of 21 randomly ascertained animals with associated factor values showed a strong correlation between genotype and factor level as presented in the histogram of FIG. 9. The shaded boxes indicate predicted genotypes based on factor levels that are not consistent with the genotypes deduced from the PCR-based diagnostic test. Larger factor value-only surveys (Johnson et al., *Vet. Clin. North Am. Small Anim. Pract.* 18:195–229 (1988); Moser et al., *Am. J. Vet. Res.* 57:1288–1293 (1996); Stokol et al., *Aust. Vet. J.* 72:257–262 (1996)) indicate substantial overlap between genotypes based upon the protein-based methods. A larger survey on 67 additional Dobermans contained in 10 independently ascertained pedigrees was performed to obtain an estimate of the mutant allele frequency within the breed. Of the total of 88 animals, 40 were AA, 35 were AG, and 13 were GG. From these results, the A allele frequency was estimated to be 0.64.

Discussion

The splice junction mutation at the end of exon 43 is the cause of recessive Type 1 vWD found within the Doberman pinscher breed. The mutation decreases the similarity between the normal splice junction and the mammalian consensus while at the same time increasing the similarity of the cryptic splice site found just upstream of the normal splice site (FIG. 6; SEQ ID NOS: 14–17). The calculated Shapiro-Senapathy splice site values (Shapiro, M. B. et al., *Nucleic Acids Res.* 15:7155 (1987)) are very similar for the normal and cryptic splice sites when an A is present at nucleotide position 7536. The Shapiro-Senapathy calculation is probably not completely accurate in determining the relative amount of splicing that can occur between different sites. Therefore, it is not inconsistent to find that the cryptic splice site is used more often than the normal site, in the mutant allele.

Figure 7:
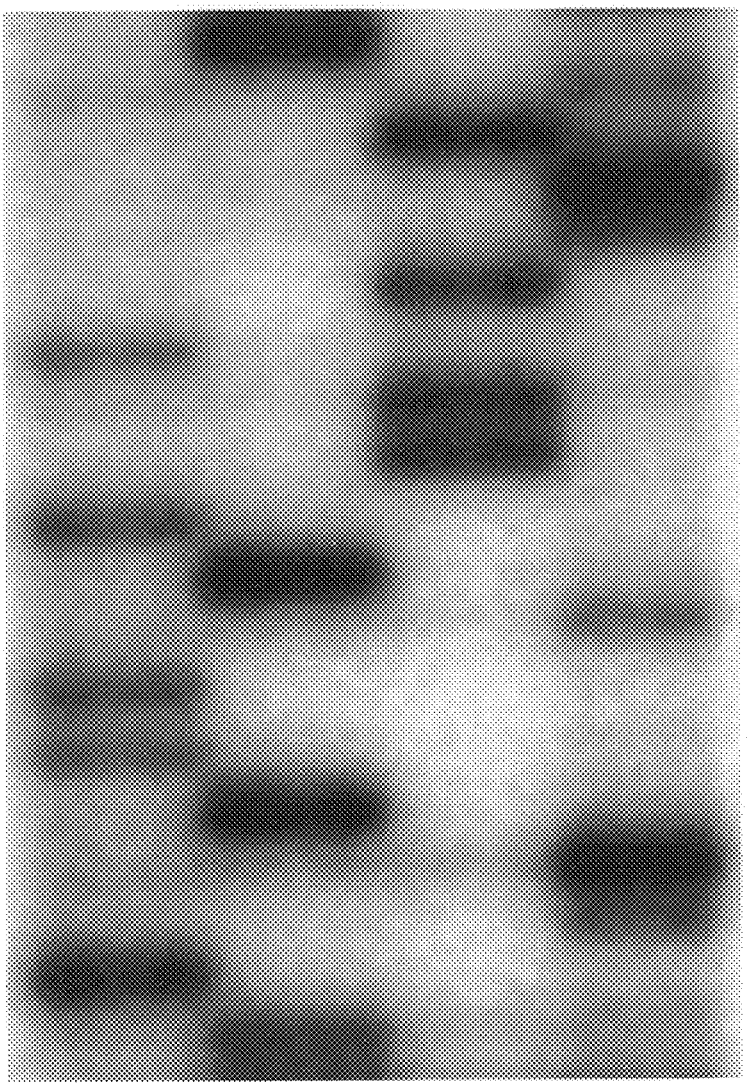
FIG. 7 is a photograph of a sequencing ladder showing the cryptic splice cite from the mutant allele (SEQ ID NO: 18)

The sequence of the minor amplification product seen just below the main amplification band exactly matches that predicted by the use of the cryptic splice site (FIG. 7; SEQ ID NO: 18). The fact that there is less cryptically spliced mRNA than normally spliced mRNA present in the cytoplasm can be explained by the relative instability of the cryptically spliced message. The cryptically spliced mRNA produces a shift in the translational reading frame, resulting in the formation of a premature stop codon. It is well known that mRNAs that produce truncated proteins are unstable, perhaps because ribosomes do not remain attached to the message to protect it from degradation by intracellular RNases or because of the incomplete assembly of splicosomes on mutant splice sites. Maquat, L. E., *Am J Hum Genet* 59:279 (1996). The average amount of vWF protein present in affected animals is roughly 10% of the normal canine value. Thus, each mutant allele should produce about 5% of the normal amount of vWF mRNA and protein. From this, it can be predicted that the average heterozygous Doberman should produce 55% of the average canine vWF value. The vWF mRNA estimated in affected animals has been shown to be roughly 20% of normal by densitometry scans of northern blots. Meinkoth, J. H. et al., *Am. J. Vet. Res.* 56:1577 (1995). This mRNA is predicted to consist primarily of the correctly spliced transcript.

Figure 9:
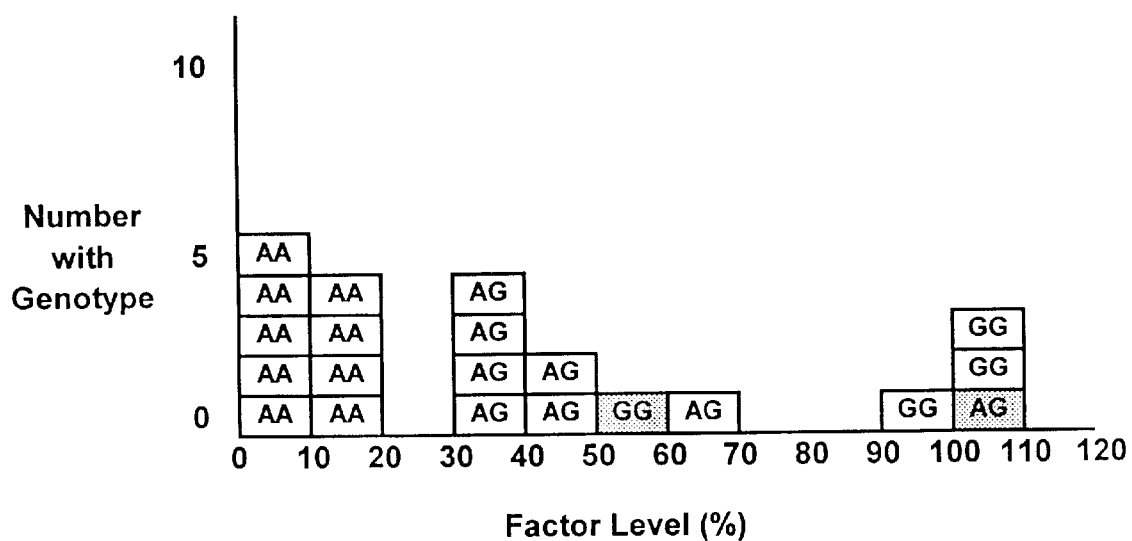
FIG. 9 is a histogram of genotypes versus reported vWF values.

The mutation has been shown to be linked to the vWF locus (FIG. 9 and Holmes, N. G. et al., *J. Small An. Prac* 37:307 (1996). Most human Type 1 vWD, in which there is a true clinical bleeding problem, appears to be inherited in a dominant, incompletely penetrant fashion. Ginsburg, D. et al., *Blood* 79:2507 (1992). Although a few Type 1 mutations have been found within the vWF locus (see, e.g., Siguret, V. et al., *Hum. Genet.* 93:95 (1994); Eikenboom, J. C. J. et al., *Blood* 88:2433 (1996)), it has been argued that another locus or loci may also cause some Type 1 vWD. Ginsburg, D. et al., *Blood* 79:2507 (1992). In fact, one murine Type 1 vWD has been mapped to locus that is not linked to the vWF gene. Nichols, W. C. et al., *Blood* 83:3225 (1994). The data show that a least a proportion of Type 1 vWD in humans might also be caused by the exon 43 mutation, or other leaky splice junction mutations. The mode of inheritance for this type of mutation is recessive, but it might appear to be dominant in certain situations, such as that of the Doberman pinscher. The number of splice site mutations of the type described herein are significantly below the number that would be predicted to occur, suggesting that these types of mutations are more difficult to detect or have been overlooked in the past. Krawcsak, M. et al., *Hum. Genet.* 90:41 (1992). This might be because they produce a less severe phenotype than other types of mutations that cause a complete loss of function.

SPECIFIC EXAMPLE 3

Shetland Sheepdog

Figure 10:
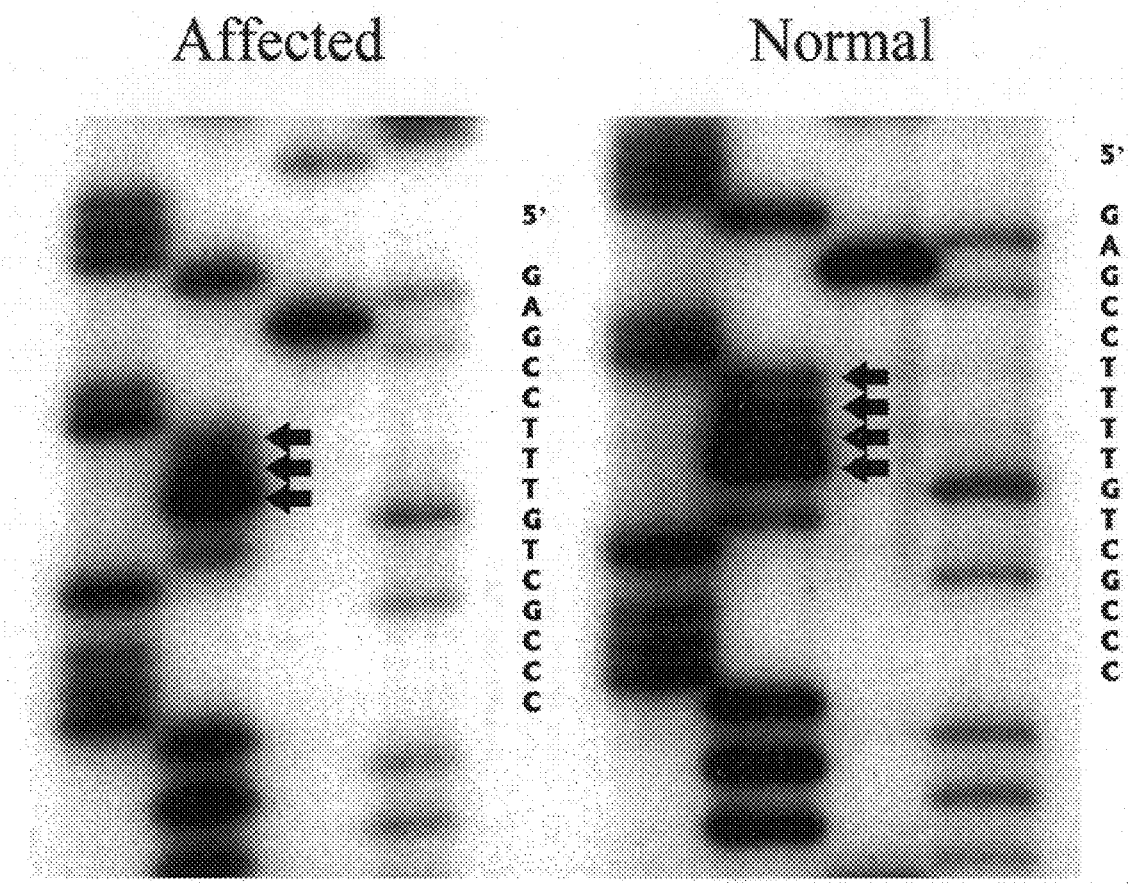
FIG. 10 is a photograph of a sequencing gel showing the mutation region between a vWD affected and a homozygous normal Shetland sheepdog (SEQ ID NOS: 19 and 20)
Figure 12:
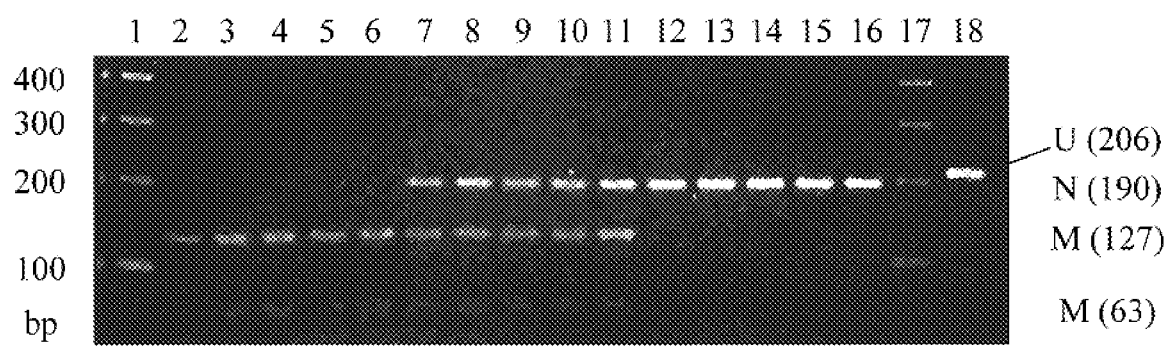
FIG. 12 is a photograph of an agarose gel showing the results of the diagnostic test for the Shetland sheepdog Type 3 vWD mutation.

Total DNA was isolated from material obtained from a spay of an affected Shetland sheepdog (Sheltie). This animal had been tested for the vWF antigen, and was reported to have a 0% value by a laboratory skilled in this testing (Diagnostic Laboratory, Comparative Hematology Section, College of Veterinary Medicine, Cornell University). The owner had decided to have the spay done after obtaining this result, and donated the removed tissues. The entire RT-PCR coding region of this mutant gene was sequenced as described in Specific Example 1, to identify the mutation that causes vWD. A mutation was found in the vWF gene that appears to be responsible for most or all of the type 3 vWD found in the Sheltie breed. A deletion of a single T was found at nucleotide position 735 of the encoding region (FIG. 10; SEQ ID NOS: 19 and 20). The arrows in FIG. 10 indicate the series of T nucleotides in which one T has been deleted in the DNA of the affected animal compared to the normal animal. This deletion, present in the equivalent of human exon 7, would cause a shift in the reading from of the vWF-encoding region, and result in a severely truncated protein. A diagnostic test was designed to detect this mutation (FIG. 11; SEQ ID NOS: 21–25). The deletion causes the creation of an Mwo I restriction site and thus, the Mwo site is found in the mutant allele, but not in the normal allele. The sequence shown in FIG. 11 (SEQ ID NOS: 21 and 22) is that of the canine gene that corresponds to the human vWF exon 7. The single letter code for amino acids is shown above the nucleotide sequence and the primer sequences are shown below the gene sequence. The Mwo I sites are also indicated. An internal digestion control site is present in the non-diagnostic primer region. Reagent concentrations for this test were: 100 μM dNTPs, 50 mM KCl, 10 mM Tris-HCl (pH 8.3), 2 mM MgCl$_2$, 0.05 to 0.1 μg target DNA, 15 μM of each primer (SEQ ID NOS: 23 and 25), and 0.025 U Taq DNA polymerase. Cycling conditions were: 94° C., 4 min, one cycle, followed by 50 cycles of 94° C., 30 sec, 63° C., 40 sec, and 72° C., 40 sec. The relatively low Taq concentration (compared to generally accepted conditions) with the high number of cycles prevents the amplification of non-specific PCR bands. One microliter of Mwo I restriction enzyme (New England Biolabs, Inc.) and 2 μl of 50 mM MgCl$_2$ were added directly to the PCR reaction after amplification, and incubated at 60° C. for 1 hr. Digestion products were then observed after gel electrophoresis on a 1.5% agarose gel and the results shown in FIG. 12. Lanes 1 and 17 show a one hundred bp ladder. Lanes 2–6 show the results from an affected animal, lanes 7–11 show the results from a carrier animal, and lanes 12–16 show the results from a homozygous normal animal. Lane 18 shows an undigested control PCR product. The duplicate samples demonstrate the reproducibility of the test. Numbers on the left side of the gel show the sizes of the standard bands, and numbers on the right side of the gel show the sizes of the uncut product (U), the normal allele (N), and the two bands for the mutant allele (M).

A survey of Shelties was conducted to determine the frequency of the mutation within the U.S. population. Of a total of 103 animals, 14 were carriers, giving a carrier frequency of 13.6%. This frequency is less than the value of 28% reported for the breed in 1988 for 730 animals when using the factor antigen test. Brooks, M. et al., *J. Am. Vet. Med. Assoc.* 200:1123–1127 (1992). One third of these carriers are thought to be due to Type 1 vWD also present in the breed. Still, the value of 13.6% would be lower than the calculated value of 18.7% from the antigen test. This difference could be due to either ascertainment biases in either study, a true decrease in the frequency of the disease in this breed, one or more additional Type 3 mutations in the breed, or a combination of these possibilities. Whatever the reason for the difference, most or all of the Type 3 disease in the Sheltie is probably caused by this one mutation. This is based on the understanding of the importance of the Founder effect (or populate sire effect) on the increase in the frequency of specific genetic diseases in purebred populations of domestic animals. A 17 member pedigree of Shelties, in which the mutation was segregating was tested for normal Mendelian inheritance of the allele. There were no differences from what would be expected under co-dominant inheritance of the two alleles.

SPECIFIC EXAMPLE 4

In an effort to find mutations that cause vWD in other canine breeds, affected animals were surveyed, as diagnosed by low levels of vWF antigen, for the three mutations set forth herein. In the case of the Manchester terrier breed, it was found that at least a portion of the affected animals had the identical mutation that causes vWD in the Doberman pinscher. The test described supra for the Doberman pinscher was utilized to test an affected Manchester terrier, plus several related animals. The affected animal was found to be homozygous for the mutant allele (Table 2). In addition, several animals who had vWF values in the carrier range were found to be carriers at the genotypic level.

TABLE 2

Manchester terrier vWF values vs. DNA genotype

| Dog | vWF value[a] | Genotype[b] |
|---|---|---|
| MT1 | 200% | normal |
| MT2 | 76% | normal |
| MT3 | 42% | carrier |
| MT4 | 19% | carrier |
| MT5 | NT | carrier |
| MT6 | NT | carrier |
| MT7 | 10% | affected |

[a]Factor values as reported from a testing lab (Cornell CVM, Hematology Lab).
[b]Genotype for the leaky splice mutation originally found in the Doberman pinscher.

SPECIFIC EXAMPLE 5

In an effort to locate mutations that cause vWD in other canine breeds, affected animals as diagnosed by low levels of vWF antigen, were surveyed for the three mutations set forth herein. The test described supra for the Doberman pinscher was utilized and, in the case of the Poodle breed, it was found that the affected animals had the identical mutation that causes vWD in the Doberman pinscher. The affected animals were found to be homozygous for the mutant allele. In addition, several animals who had vWF values in the carrier range were found to be carriers at the genotypic level.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All patents and other publications cited herein are expressly incorporated by reference.

We claim:

1. An isolated nucleic acid molecule comprising a nucleotide sequence encoding mutated canine von Willebrand Factor polypeptide which causes canine von Willebrand's disease, wherein the nucleotide sequence is capable of hybridizing under high stringency conditions to the complementary sequence of the sequence of SEQ ID NO. 1 having a mutation at nucleotide 7639.

2. A vector comprising the nucleic acid molecule of claim 1.

3. A cell comprising the vector of claim 2.

4. The isolated nucleic acid molecule of claim 1, wherein the mutation at nucleotide 7639 is a substitution.

5. A method of detecting a canine von Willebrand Factor gene in a sample comprising the steps of:
   a) contacting the sample with an oligonucleotide comprising contiguous nucleotides of the nucleic acid sequence of SEQ ID NO. 1 or complement thereof, having a mutation at nucleotide 7639, and capable of specifically hybridizing with the canine von Willebrand Factor gene, under conditions favorable for hybridization of the oligonucleotide to any complementary sequence of nucleic acid in the sample; and
   b) detecting hybridization, thereby detecting a canine von Willebrand Factor gene.

6. The method of claim 5, further comprising the step of:
   c) quantifying hybridization of the oligonucleotide to the complementary sequence.

7. The method of claim 5, wherein the mutation at nucleotide 7639 is a substitution.

8. An assay kit for screening for a canine von Willebrand Factor gene comprising:
   a) an oligonucleotide comprising contiguous nucleotides of the nucleic acid sequence of SEQ ID NO. 1 having a mutation at nucleotide 7639, and capable of hybridizing with the nucleotide sequence encoding canine von Willebrand Factor;
   b) reagents for hybridization of the oligonucleotide to a complementary nucleic acid sequence; and
   c) container means for a)–b).

9. The assay kit of claim 8, wherein the mutation at nucleotide 7639 is a substitution.

10. An assay kit for screening for a canine von Willebrand Factor gene comprising:
    a) an oligonucleotide comprising contiguous nucleotides of the nucleic acid sequence that is complementary to the sequence of SEQ ID NO. 1 having a mutation at nucleotide 7639, and capable of specifically hybridizing to the complementary nucleotide sequence;
    b) reagents for hybridization of the oligonucleotide to a complementary nucleic acid sequence; and
    c) container means for a)–b).

11. The assay kit of claim 10, wherein the mutation at nucleotide 7639 is a substitution.

12. A method for detecting a mutated canine von Willebrand Factor gene in a canine DNA sample comprising the steps of:
    a) amplifying the DNA sample by polymerase chain reaction to produce polymerase chain reaction products, wherein the polymerase chain reaction uses primers that produce a restriction site in a mutant allele but not in a normal allele, wherein the mutation in the mutant allele is a substitution at nucleotide 7639 of the nucleotide sequence encoding canine von Willebrand Factor polypeptide, wherein the nucleotide sequence is capable of hybridizing under high stringency conditions to the complementary sequence of the sequence of SEQ ID NO. 1;
    b) digesting the polymerase chain reaction products with a restriction enzyme specific to the restriction site of the restriction site primer to produce DNA fragments; and
    c) detecting the DNA fragments, thereby detecting a mutated canine von Willebrand Factor gene.

13. The method of claim 12, wherein the DNA fragments are detected by gel electrophoresis.

14. The method of claim 12, wherein the primers comprise the sequence of SEQ ID NOS: 28 and 29.

15. The method of claim 12, wherein the restriction enzyme is Msp I.

16. An oligonucleotide probe capable of detecting a mutation associated with canine von Willebrand's disease, wherein the mutation is a base substitution at nucleotide 7639 of the nucleotide sequence encoding canine von Willebrand Factor polypeptide, wherein the nucleotide sequence is capable of hybridizing under high stringency conditions to the complementary sequence of the sequence of SEQ ID NO. 1.

17. The oligonucleotide probe of claim 16, wherein the substitution at nucleotide 7639 is adenine for guanine.

* * * * *

UNITED STATES PATENT AND TRADEMARK OFFICE
CERTIFICATE OF CORRECTION

PATENT NO. : 6,074,832 Page 1 of 1
DATED : June 13, 2000
INVENTOR(S) : Patrick J. Venta et al.

It is certified that error appears in the above-identified patent and that said Letters Patent is hereby corrected as shown below:

<u>Title page,</u>
Item [73], Assignee should read:

-- [73] Assignees: The Regents of the University of Michigan, Ann Arbor, Michigan and Board of Trustees operating Michigan State Unversity, East Lansing, Michigan --

Signed and Sealed this

Fourteenth Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,074,832  
APPLICATION NO. : 09/132652  
DATED : June 13, 2000  
INVENTOR(S) : Patrick J. Venta et al.

Page 1 of 1

It is certified that error appears in the above-identified patent and that said Letters Patent is hereby corrected as shown below:

On the Title Page  Please remove inventor John Duffendeck

Signed and Sealed this

Fourteenth Day of October, 2008

JON W. DUDAS  
*Director of the United States Patent and Trademark Office*